US011737896B2

(12) United States Patent
Bhamra et al.

(10) Patent No.: US 11,737,896 B2
(45) Date of Patent: Aug. 29, 2023

(54) WIRELESSLY-POWERED IMPLANTABLE EMG RECORDING SYSTEM

(71) Applicant: Purdue Research Foundation, West Lafayette, IN (US)

(72) Inventors: Hansraj Singh Bhamra, West Lafayette, IN (US); Jimin Maeng, West Lafayette, IN (US); Chuizhou Meng, West Lafayette, IN (US); Rebecca Bercich, Minneapolis, MN (US); Oren Gall, Lafayette, IN (US); Young-Joon Kim, West Lafayette, IN (US); Jithin Joseph, Mountain View, CA (US); William Chappell, Vienna, VA (US); Pedro Irazoqui, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 706 days.

(21) Appl. No.: 13/955,808

(22) Filed: Jul. 31, 2013

(65) Prior Publication Data

US 2014/0088379 A1    Mar. 27, 2014

Related U.S. Application Data

(60) Provisional application No. 61/677,952, filed on Jul. 31, 2012.

(51) Int. Cl.
*A61B 5/07* (2006.01)
*A61F 2/72* (2006.01)

(52) U.S. Cl.
CPC ............... *A61F 2/72* (2013.01); *A61B 5/076* (2013.01); *A61B 2560/0209* (2013.01); *A61B 2560/0219* (2013.01)

(58) Field of Classification Search
CPC ............... A61B 5/04888; A61B 5/076; A61B 2560/0209; A61B 2560/0219; A61F 2/72
See application file for complete search history.

(56) References Cited

U.S. PATENT DOCUMENTS

| | | | |
|---|---|---|---|
| 6,411,842 B1 | 6/2002 | Cigaina et al. | |
| 6,735,474 B1* | 5/2004 | Loeb | A61N 1/36007 607/41 |
| 6,970,741 B1* | 11/2005 | Whitehurst | A61B 5/053 128/899 |
| 7,478,009 B2* | 1/2009 | Cabrera | A61B 5/1107 482/6 |

(Continued)

FOREIGN PATENT DOCUMENTS

| | | |
|---|---|---|
| EP | 1274345 | 10/2007 |
| WO | 2007047954 | 4/2007 |

(Continued)

OTHER PUBLICATIONS

US 8,388,533 B2, 03/2013, Costello et al. (withdrawn)

(Continued)

*Primary Examiner* — Navin Natnithithadha
(74) *Attorney, Agent, or Firm* — Piroozi-IP, LLC

(57) ABSTRACT

Apparatus and methods for the measurement and transmission of data pertaining to the tissue of an animal. In one embodiment, there is an implantable device that is wirelessly powered and also wirelessly transmits data. Preferably, the implant measures neuromuscular activity.

39 Claims, 23 Drawing Sheets

(56) References Cited

U.S. PATENT DOCUMENTS

| | | |
|---|---|---|
| 7,658,119 B2 | 2/2010 | Loeb et al. |
| 7,720,547 B2 | 5/2010 | Denker et al. |
| 7,878,075 B2 | 2/2011 | Johansson et al. |
| 7,908,014 B2 | 3/2011 | Schulman et al. |
| 7,978,064 B2 | 7/2011 | Zdeblick et al. |
| 8,036,748 B2 | 10/2011 | Zdeblick et al. |
| 8,038,601 B2 | 10/2011 | Shimizu et al. |
| 8,054,140 B2 | 11/2011 | Fleming et al. |
| 8,055,334 B2 | 11/2011 | Savage et al. |
| 8,114,021 B2 * | 2/2012 | Robertson ............ A61B 5/0006 600/300 |
| 8,115,618 B2 | 2/2012 | Colliou et al. |
| 8,115,635 B2 | 2/2012 | Goodnow et al. |
| 8,181,540 B2 | 5/2012 | Loeb et al. |
| 8,223,021 B2 | 7/2012 | Goodnow et al. |
| 8,258,962 B2 | 9/2012 | Robertson et al. |
| 8,272,278 B2 | 9/2012 | Loeb et al. |
| 8,358,210 B2 | 1/2013 | Goodnow et al. |
| 8,390,455 B2 | 3/2013 | Goodnow et al. |
| 8,412,352 B2 | 4/2013 | Griswold et al. |
| 8,515,559 B2 | 8/2013 | Griswold et al. |
| 8,540,632 B2 | 9/2013 | Robertson et al. |
| 8,540,633 B2 | 9/2013 | Hafezi et al. |
| 8,540,664 B2 | 9/2013 | Robertson et al. |
| 8,542,122 B2 | 9/2013 | Goodnow et al. |
| 8,542,123 B2 | 9/2013 | Zdeblick et al. |
| 8,545,402 B2 | 10/2013 | Hafezi et al. |
| 8,545,436 B2 | 10/2013 | Hafezi et al. |
| 8,547,248 B2 | 10/2013 | Zdeblick et al. |
| 8,558,563 B2 | 10/2013 | Zdeblick et al. |
| 8,583,227 B2 | 11/2013 | Savage et al. |
| 8,594,785 B2 | 11/2013 | Bradley |
| 8,597,186 B2 | 12/2013 | Hafezi et al. |
| 2003/0114769 A1 | 6/2003 | Loeb et al. |
| 2006/0129056 A1 * | 6/2006 | Leuthardt ............ A61B 5/0006 600/544 |
| 2006/0161225 A1 | 7/2006 | Sormann et al. |
| 2006/0206167 A1 | 9/2006 | Flaherty et al. |
| 2006/0265039 A1 * | 11/2006 | Bartic ................ A61N 1/0531 607/116 |
| 2007/0156126 A1 * | 7/2007 | Flaherty ............ A61B 5/0084 606/32 |
| 2008/0077188 A1 * | 3/2008 | Denker ................ A61N 1/372 607/17 |
| 2009/0157141 A1 * | 6/2009 | Chiao ................ A61N 1/36071 607/46 |
| 2009/0157145 A1 * | 6/2009 | Cauller ............... A61B 5/04001 607/60 |
| 2010/0081895 A1 | 4/2010 | Zand |
| 2011/0257715 A1 | 10/2011 | Jarach et al. |
| 2011/0301716 A1 * | 12/2011 | Sirivisoot ............... A61L 27/50 623/23.53 |
| 2012/0197342 A1 | 8/2012 | Towe |
| 2013/0289363 A1 * | 10/2013 | Addington ......... A61B 5/04882 600/301 |

FOREIGN PATENT DOCUMENTS

| | | |
|---|---|---|
| WO | 2007050413 | 5/2007 |
| WO | 2008144578 | 11/2008 |
| WO | 2009023334 | 2/2009 |
| WO | 2009026499 | 2/2009 |
| WO | 2010063024 | 6/2010 |
| WO | 2010065604 | 6/2010 |
| WO | 2010081134 | 7/2010 |
| WO | 2010083228 | 7/2010 |
| WO | 0113778 | 3/2011 |
| WO | 2010141603 | 3/2011 |
| WO | 2011084450 | 7/2011 |
| WO | 2013063111 | 5/2013 |

OTHER PUBLICATIONS

US 8,469,885 B2, 06/2013, Costello et al. (withdrawn)
US 8,469,921 B2, 06/2013, Robertson et al. (withdrawn)
US 8,480,616 B2, 07/2013, Robertson et al. (withdrawn)
EP Lab, Electrograms—Electrode Spacing, 2010, Web, Retrieved from: http://www.theeplab.com/B-The-Members-Center/A000-Electrograms/A-Electrograms/C-Electrode-Spacing/DA20-Electrode-Spacing.php.*
Farnsworth, Wireless Implantable EMG Sensing Microsystem, 2010, Electronic Thesis, Retrieved from: https://etd.ohiolink.edu/pg_10?0::NO:10:P10_ACCESSION_NUM:case1276263665.*
Ortiz-Catalan et al, On the viability of implantable electrodes for the natural control of artificial limbs: Review and discussion, 2012, BioMedical Engineering OnLine, 11(33): pp. 1-24.*

* cited by examiner

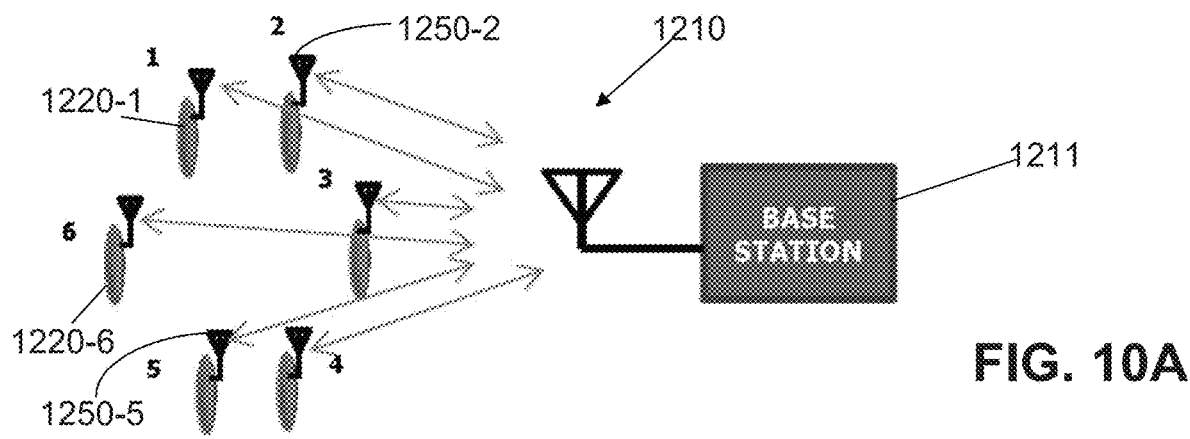
FIG. 10A
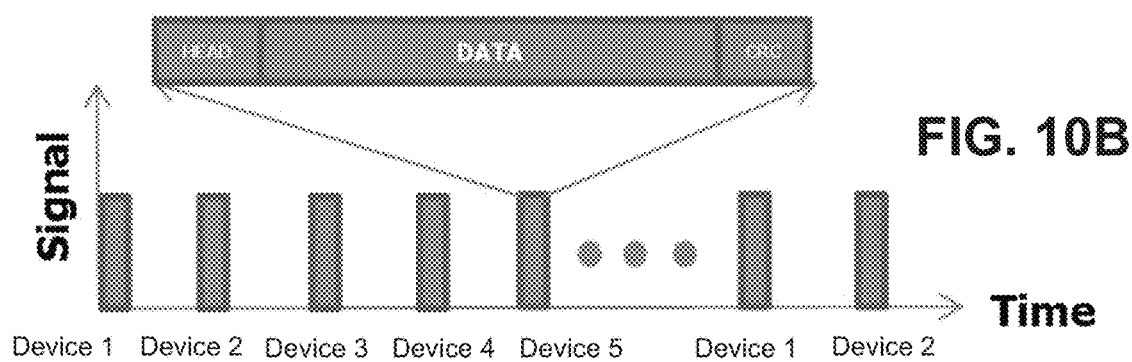
FIG. 10B
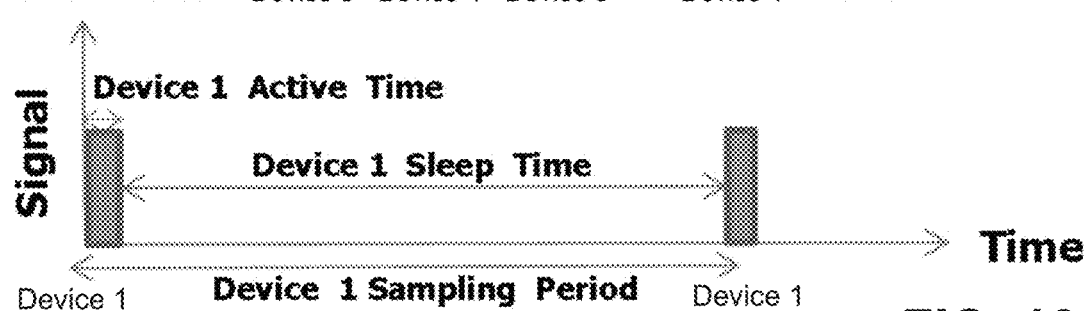
FIG. 10C
FIG. 10

WIRELESSLY-POWERED IMPLANTABLE EMG RECORDING SYSTEM

CROSS REFERENCED TO RELATED APPLICATION

This application claims the benefit of priority to U.S. Provisional Patent Application Ser. No. 61/677,952, filed Jul. 31, 2012, incorporated herein by reference.

FIELD OF THE INVENTION

Various embodiments pertain to device implantable in an animal for measurement of tissue data, and in particular to the measurement of electrical activity in an animal muscle.

BACKGROUND OF THE INVENTION

The loss of an arm is a major disability that profoundly limits the everyday capabilities and interactions of upper-limb amputees. The impairment of bimanual dexterity limits employment opportunities and can impede routine activities such as driving and cleaning. Difficulty in holding objects also impedes leisure activities such as reading or playing sports. Upper-limb amputation even interferes with basic activities of daily living including dressing, eating, and personal hygiene. The disability is magnified with bilateral arm amputation and can threaten a person's basic independence. The majority of upper-limb amputations are due to trauma and happen to relatively young and active individuals; therefore, the majority of upper-limb amputees are otherwise active and able individuals who must live with their disability for many years. Despite these facts, the market for upper-limb prostheses is not usually large enough to motivate a large development effort.

Currently available prostheses do not adequately restore the function of lost arms. The most commonly used prostheses are body-powered. These devices capture remaining shoulder motion with a harness and transfer this movement through a cable to operate the elbow, wrist, or terminal device. One joint can be operated at a time, and a switch must be operated to change functions. Myoelectric prostheses use the electromyogram (EMG) signals (the electrical signals generated during a muscle contraction) from one or two residual-limb muscles to control motorized arm components. Various switching techniques, such as muscle co-contraction, are used to change functions. This type of operation is awkward and not intuitive, as control and switching require unnatural muscle contractions. Perhaps the strongest testament to the inadequacy of upper-limb prostheses is that 50% of patients with an upper-limb amputation use a prosthesis. While some advances have been made in recent years to build stronger and perhaps more versatile upper-limb prostheses, little progress is being made on improving the control of artificial arms.

Targeted reinnervation is a proven technique for providing increased neural control information with a low-risk, one-time surgery. During the surgery, residual nerves are routed to spare muscle sites. When the muscles have been reinnervated, natural movement attempts of the missing limb produce muscle contractions that can be sensed by surface electrodes and used to control a multifunctional arm. The patient can operate both their hand and elbow, simultaneously, with intuitive control. Targeted reinnervation has been successfully performed in over 50 people with upper-limb amputations worldwide and is now a growing clinical option for patients with upper-limb amputations.

Another technology has been demonstrated to improve prosthesis control and function in the lab—pattern recognition control. Pattern recognition algorithms can decode EMG signals to provide intuitive control of multiple powered prosthetic joints—if there is adequate data in the signals. With pattern recognition, the system learns to identify the patterns of muscle activity elicited when a user attempts a movement with the residual limb, and operates the prosthesis based on the real-time recognition of these patterns. We have demonstrated that transradial amputees can use pattern recognition control with surface EMG signals to operate wrist rotation, wrist flexion, wrist extension and multifunction hands. When pattern recognition is combined with targeted muscle reinnervation (TMR), a powered elbow can also be controlled. With shoulder disarticulation TMR patients, humeral rotation can also be controlled with EMG and a powered shoulder can also be operated with mechanical transducers.

The success of both TMR and pattern-recognition control is, however, limited by the variability in recorded EMG signals. Movement of electrodes and changes in skin moisture can significantly change the EMG signals and degrade the control of the device. This significantly impairs the robustness of these technologies. Furthermore, the EMG changes and limit the patient from optimally learning their control system since it is constantly changing as the EMG changes. Using surface EMG signals also demands a tight socket fit to hold the electrodes to the skin and in the same position, as well as possible. Having to have such a tight fit is less comfortable to the patient and making donning the prosthesis a significant hassle.

Most state-of-the-art upper-limb prostheses utilize myoelectric (EMG) signals in order to control functionality. These signals are often retrieved at the surface of the skin, leading to poor spatial and temporal resolution. In order to take full advantage of the information provided by the residual and reinnervated muscles of upper-limb amputees, some means must be devised to retrieve consistent, predictable, and independent EMG signals. Stable, independent channels of myoelectric information are particularly useful when pattern recognition is the chosen control paradigm for prosthetic function.

The various inventions disclosed herein provide novel and nonobvious apparatus and methods for improving the control of powered prosthetic devices.

SUMMARY OF THE INVENTION

Various embodiments of the present invention pertain to improvements in the measurement and use of electromyogram (EMG) devices.

Some embodiments pertain to an EMG sensor implantable within the muscles of an animal. Preferably, the sensor includes two electrodes that are spaced apart from one another. Preferably, this sensor has a generally smooth overall shape that is adapted and configured for long term implantation. In some embodiments, the electrodes are smoothly integrated into the outer shape of the sensor assembly.

Yet other embodiments of the present invention pertain to an EMG sensor that is adapted and configured to be implanted into the body of an animal so as to detect electromyogram signals. In some embodiments, the sensor includes a radio frequency antenna adapted and configured to transmit and receive data, and further configured to receive electromagnetic energy in the gigahertz range. In some embodiments, the antenna is adapted and configured to be located closer to the skin than the sensor external package.

Yet other embodiments of the present invention pertain to the detection, storage, and transmission of data pertaining to EMG signals using circuit topology that uses very little power. In some embodiments, there is an EMG sensor that includes an application specific circuit (ASC) having a power consumption of less than about seven hundred microwatts. In some embodiments the ASC includes a power amplifier that reuses current of a voltage-controlled oscillator, so as to improve transmitter operation and stabilize the load characteristics of the antenna. In yet other embodiments the EMG data is recorded on the ASC and transmitted in bursts to reduce power for transmission of date. Yet other embodiments of the present invention pertain to an EMG sensor that receives power when implanted in an animal by wireless means, such as radio frequency or induction. The waveform of the RF power or the induced power is adapted and configured to provide efficient conversion of the power to the types of voltages to operate an ASIC. In some embodiments the radio frequency power or the induced power is attached and configured to be provided in a pulsatile manner so as to more efficiency drive various semiconductors, such as rectifying diodes.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting. Some of the schematic drawings include standard electrical symbology.

FIG. 10A is a schematic representation of a system of implantable devices in a base station according to one embodiment of the present invention showing a possible duty cycle.

FIG. 10B is a temporal representation of a communication protocol for the system of FIG. 10A, according to one embodiment of the present invention.

FIG. 10C is a temporal representation of a strategy for operation of an implantable device of FIG. 10A.

ELEMENT NUMBERING

Figure 1A:
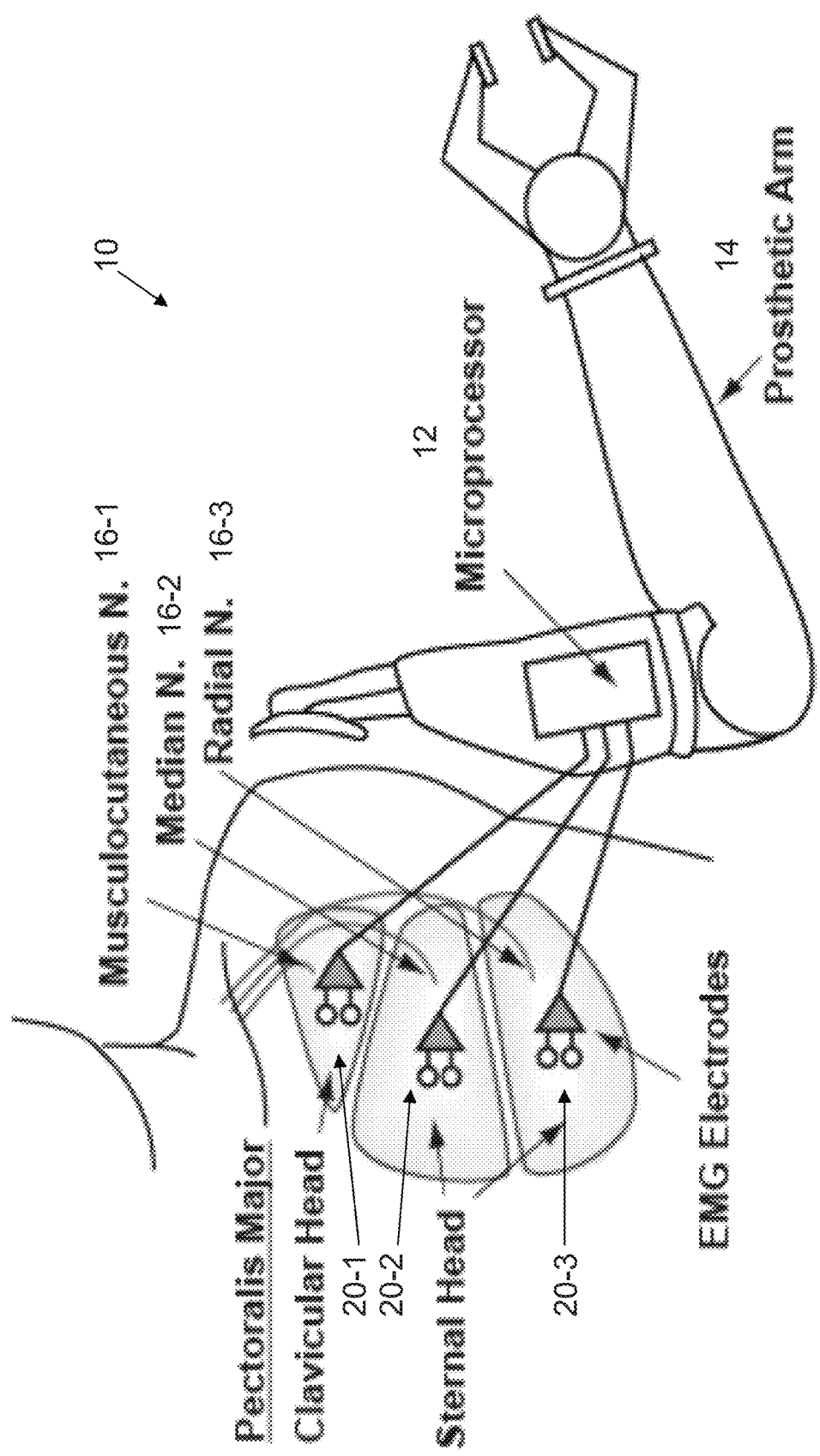
FIG. 1A is a schematic representation of a system for controlling a device according to one embodiment of the present invention.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| 10 | EMG system |
|----|------------|
| 11 | base station |

-continued

| | |
|---|---|
| 12 | controller, external |
| 14 | controlled device |
| 16 | muscle, nerve |
| 18 | insertion tool; trochanter |
| 19 | external interface; iPad |
| 20 | implanted device |
| 22 | substrate, parylene |
| 24 | closure, parylene |
| 30 | electrode |
| a | first electrode |
| b | second electrode |
| 40 | application specific integrated circuit (ASIC) |
| 50 | antenna |
| a | power receiving |
| b | signal transmitting |
| 52 | rectifier, RF |
| 54 | matching network |
| 55 | frequency divider |
| 60 | generator |
| 62 | antenna, power transmitting |
| 70 | power supply |
| 72 | battery |
| 74 | capacitor, regular |
| 76 | supercapacitor |
| 77 | electrodes |
| 78 | boost converter, charge pump |

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments.

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology.

Further, it is understood that the features 1020.1 and 20.1 may be backward compatible, such that a feature (NXX.XX) may include features compatible with other various embodiments (MXX.XX), as would be understood by those of ordinary skill in the art. This description convention also applies to the use of prime ('), double prime ("), and triple prime ("') suffixed element numbers. Therefore, it is not necessary to describe the features of 20.1, 20.1', 20.1", and 20.1'" that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

What will be shown and described herein, along with various embodiments of the present invention, is discussion of one or more tests that were performed. It is understood that such examples are by way of example only, and are not to be construed as being limitations on any embodiment of the present invention. Further, it is understood that embodiments of the present invention are not necessarily limited to or described by the mathematical analysis presented herein.

Various references may be made to one or more processes, algorithms, operational methods, or logic, accompanied by a diagram showing such organized in a particular sequence. It is understood that the order of such a sequence is by example only, and is not intended to be limiting on any embodiment of the invention.

An implantable electrode fashioned specifically for EMG detection and transmission could provide the necessary recording stability which would drastically improve the performance of myoelectric controlled prostheses. By implanting these sensors permanently into residual muscle, many of the challenges faced by surface EMG electrodes (changing skin conditions, shifting of the prosthetic socket, daily recalibration as the prosthetic is removed and re-attached) can be overcome. By providing more reliable channels of motor control information, prostheses can achieve greater functionality and amputees can attain a better quality of life.

Various embodiments of the present invention pertain to implantable modules or medical devices that measure tissue activity of an animal. In some embodiments, these devices measure neuromuscular voltages, and can be used within a system for the control of a prosthetic device, as diagnostic data for use in treating the patient, or for any other purpose. Further, although reference will be made herein to the measurement of voltages by one or more electrodes that have pads external to the body of the implanted device, it is further understood that in yet other embodiments these device-external pads can be electrochemical sensors adapted and configured to produce a signal corresponding to the presence of a chemical in the tissue in of the animal.

In yet other embodiments, there is a system in which a plurality of devices or modules measure neuromuscular activity. In such systems, preferably, all modules perform EMG recording. They receive sufficient power and secure data transmission to function reliably when the prosthesis is adequately positioned on the body of the patient. Multiple modules are able to be implantable in different locations and orientations. Modules should not respond to electromagnetic fields that might be produced by consumer or other medical electronic equipment. Power without wires can be provided by a continuously present electromagnetic field. Because the modules can be used for many hours per day while they are in proximity to a source of power in the prosthetic limb, in one embodiment the modules are powered continuously from an external electromagnetic field, with no battery or power storage other than filter capacitors in the modules.

Figure 1B:
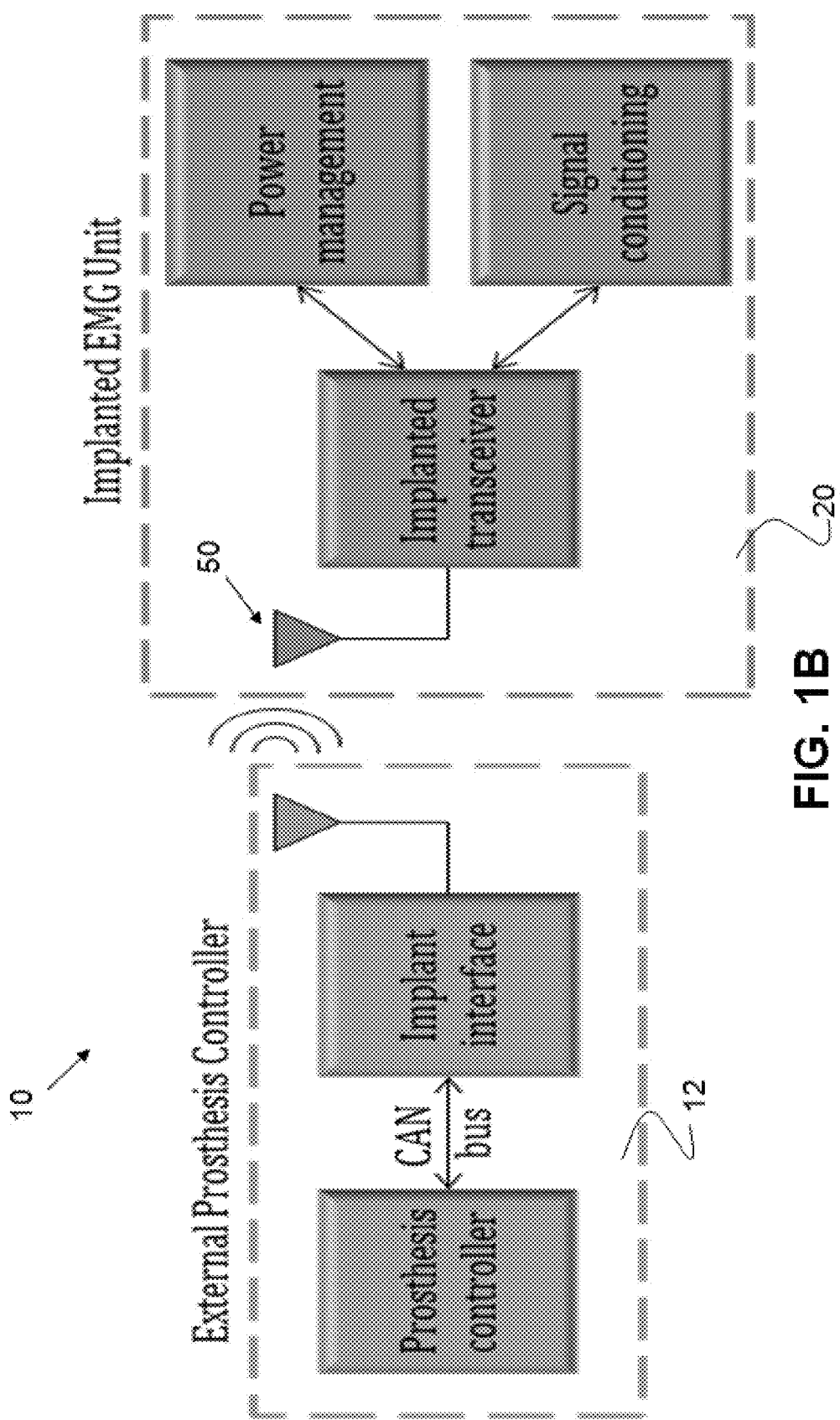
FIG. 1B is a block diagram of a system according to one embodiment of the present invention.
Figure 1C:
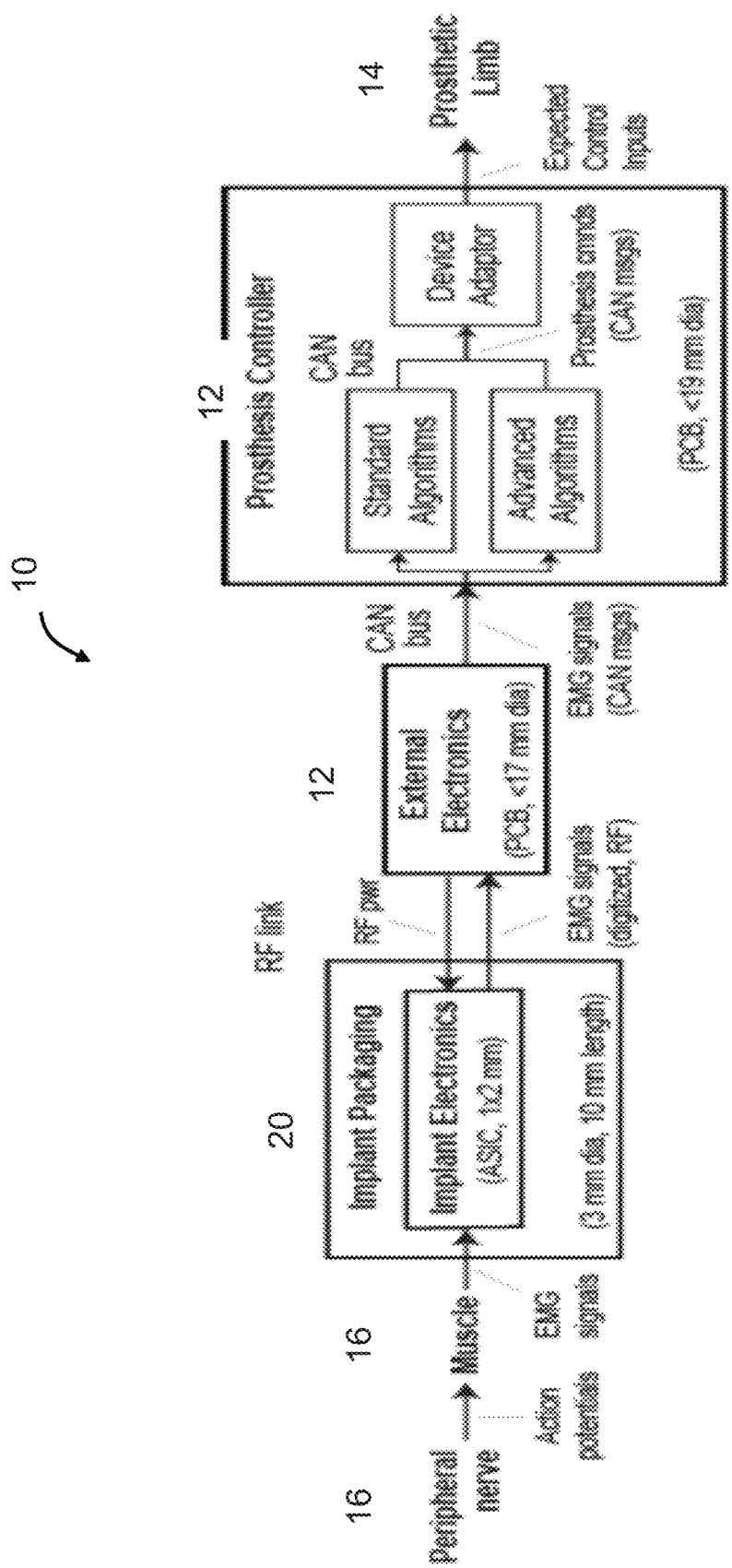
FIG. 1C is a block diagram of a system according to one embodiment of the present invention.

An intramuscular EMG (IEMG) system 10 as shown in FIGS. 1A, 1B, and 1C could alleviate many of the problems of surface EMG and also further improve prosthesis control. Implanted electrodes 20 would not move, thus the EMG signals would be consistent from hour to hour and day to day, and possibly more robust than surface EMG. As compared to surface electrodes the prosthetic socket should not be as tight, and therefore more comfortable and easier to don and doff. Eliminating the surface electrodes would remove a constraint from socket and liner designs—the skin would be free to use any desired materials. IEMG signals would also allow more focal recording from muscles and the ability to record independent signals from deep muscles. This could improve the control of the prosthesis. It is possible the IEMG electrodes could be placed in wrist, finger and thumb muscle enabling independent and simultaneous control of the wrist and a multifunction prosthetic hand; possibly even fingers and thumbs.

One embodiment increases the fidelity, reliability, and robustness of upper limb prosthesis control, while providing flexibility in the choice of prosthetic components and immediate deployment capability. The system can use low-power radio frequency (RF) technology. This will facilitate reliable, long-term stable recording of EMG signals and improvements in prosthesis control. The technology will be used using surface electrodes in individuals who have had the targeted muscle reinnervation procedure, and could benefit myoelectric prosthesis users.

One proposed application of an implantable EMG system 10 is for control 12 of a powered prostheses as shown in FIG. 1A. One possible use for the proposed implantable EMG systems is transradial amputees and higher level amputees that have had Targeted Muscle Reinnervation Surgery. The transradial amputees should have a residual limb length of about 4 cm from the elbow crease as the shortest limbs. The limb should be long enough to adequately fit with a prosthesis and have adequate residual muscle. Long transradial amputees could be fit to any length. Very long transradial and wrist disarticulation patients would have to decide how long of a prosthesis they would accept. Higher level patients (transhumeral and shoulder disarticulation amputees) with TMR surgery would also be an application for the IEMG system. Patients that can be fit with a powered prosthesis would be considered candidates One aspect of the EMG telemetry modules is to obtain independent signals from several regions (hereafter referred to as "channels"). The spacing and orientation of the electrodes 30 of each module 20 are designed to sample these functional regions.

FIG. 1A schematically shows a person with a prosthetic, control device 14 such as an arm. This prosthetic device operates under the control of a microprocessor 12 that receives signals from a plurality of implanted devices 20, which in one embodiment are EMG devices incorporating electrodes. It can be seen that this user includes three implanted devices 20, with a first device 20-1 receiving neuromuscular signals from the musculocutaneous nerve 16-1. A second implanted device 20-2 receives neuromuscular signals from a median nerve 16-2. A third implanted device 20-3 receives neuromuscular signals from a radial nerve 16-3. Each of these implanted devices provides a wireless data stream to microprocessor 12, this data being analyzed by the microprocessor as driving inputs to the various actuators of prosthetic arm 14.

FIG. 1B shows the system of FIG. 1A in block diagram form, with the prosthetic controller 12 communicating via a CAN bus with an implant transceiver. In some embodiments, the transceiver of the external controller provides both a power signal to the implant 20, and further receives a data stream from the implant 20. Power can be transmitted to the implant by a variety of means, but in some embodiments is by way of a radio frequency signal.

FIG. 1B further shows that implanted device 20 receives the signal by way of an implanted antenna 50. This signal is used to provide power to the implant, and further, this antenna can be used by an implanted transmitter to transmit data. FIG. 1C describes further aspects of a prosthetic EMG system 10 according to one embodiment of the present invention.

Figure 2A:
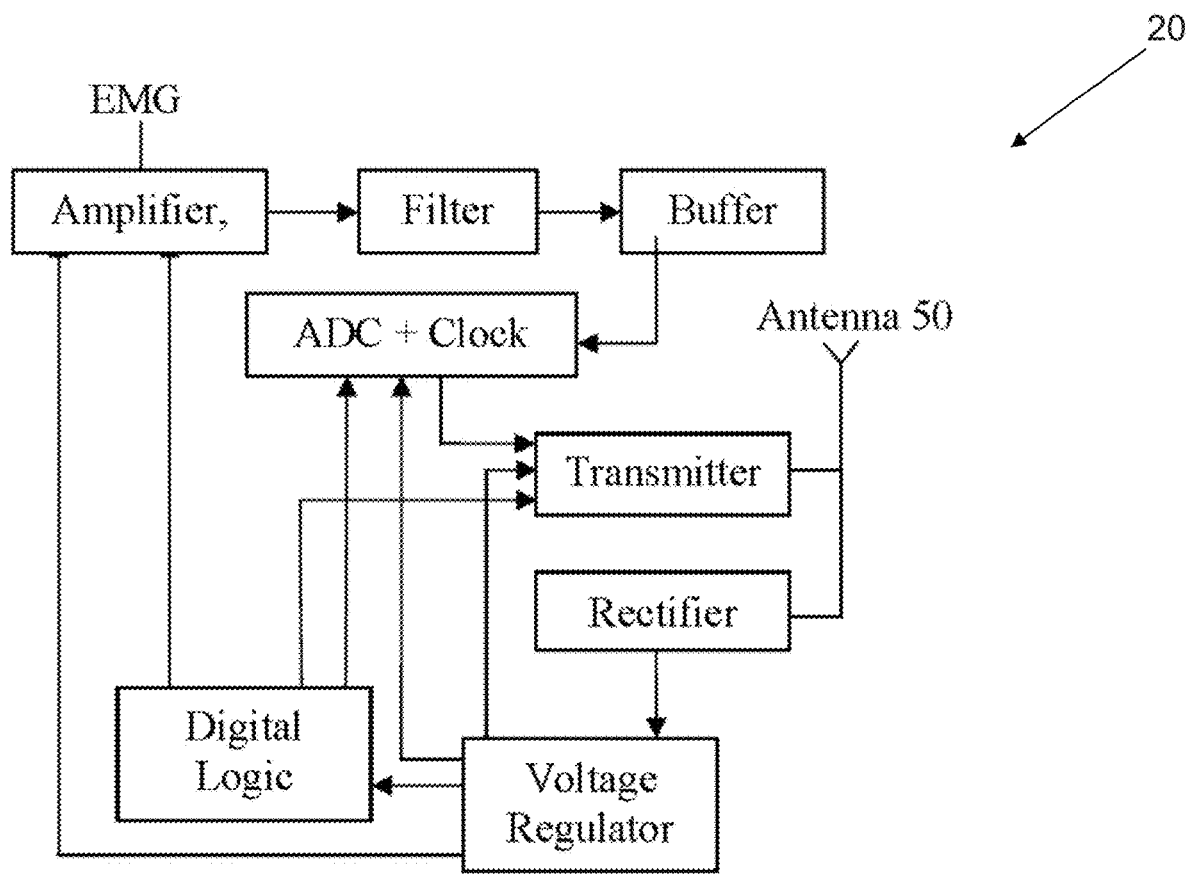
FIG. 2A is a block diagram of an implanted probe according to one embodiment of the present invention.
Figure 2B:
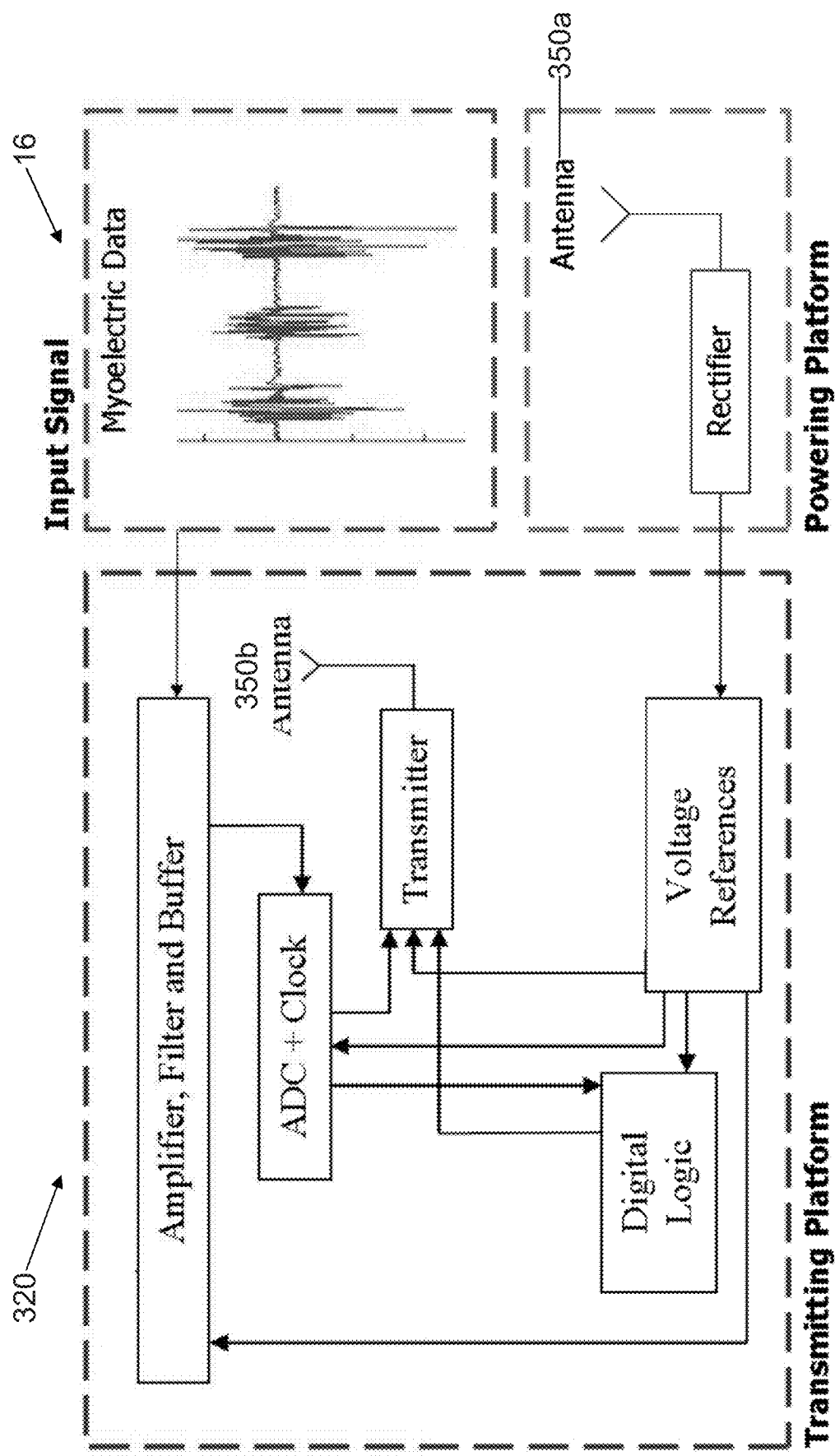
FIG. 2B is a block diagram of a portion of a system according to another embodiment of the present invention.
Figure 2C:
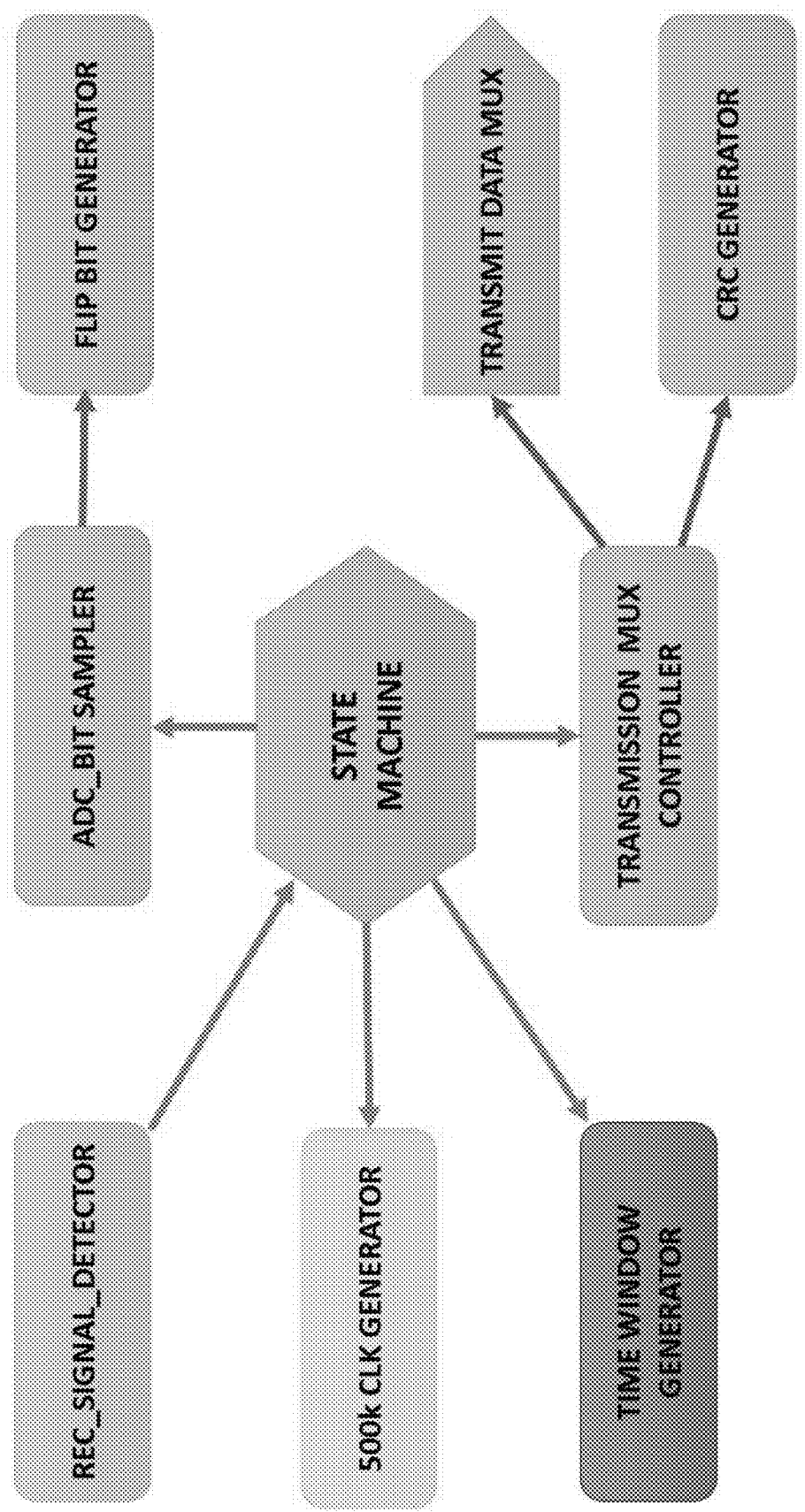
FIG. 2C is a logic block diagram according to another embodiment of the present invention.

FIGS. 2A and 2B include block diagrams of implantable devices 20 and 320 according to various embodiments of the present invention. It can be seen that implanted device 20 includes a single antenna 50 that provides an electrical signal to a rectifier and voltage regulator that can be used to power the various electrical components of the implanted device. Preferably, power from the rectifier is provided to one or more internal batteries or capacitors that subsequently provide power through the voltage regulator for the device circuitry. In some embodiments, radiated power received on antenna 50 is rectified and stored in capacitors, and in some embodiments by a combination of dielectric-effect capacitors and surface absorption capacitors, as will be discussed later.

In addition, antenna 50 receives encoded information from an implanted transmitter that represents data about the various neuromuscular signals acquired by the implant 20. In some embodiments, antenna 50 is adapted and configured to receive power at a first predetermined radio frequency, and to broadcast data at a second predetermined frequency that is a harmonic of the first frequency. However, various embodiments of the present invention including device 320 include a pair of antennas 350. A first antenna 350b is adapted and configured to transmit encoded data at a first predetermined ratio frequency. Antenna 350a is adapted and configured to receive radiated radio frequency power at a second predetermined frequency, this radiated power being rectified for subsequent use in driving various components of implanted device 320.

Figure 3:
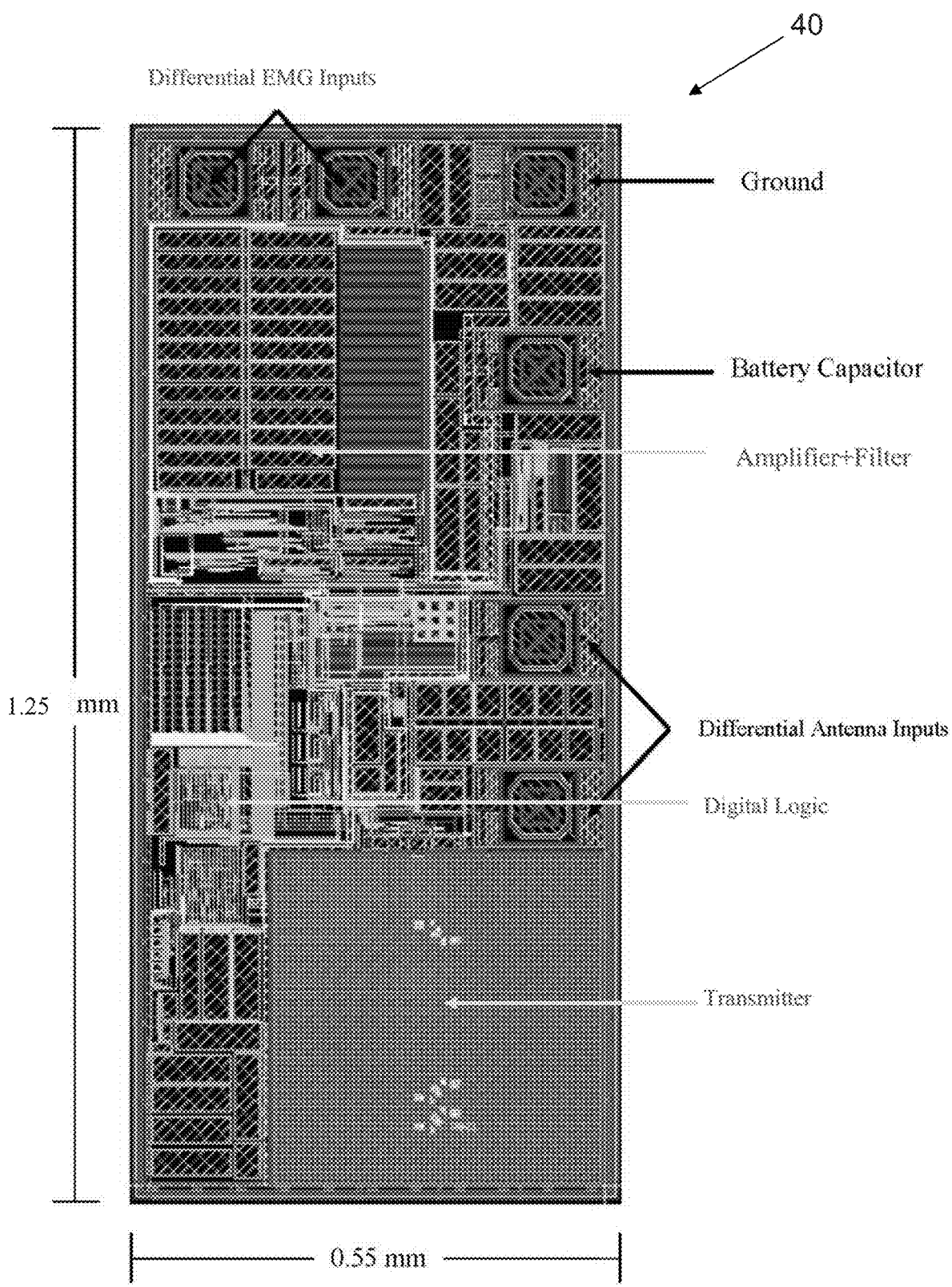
FIG. 3 is a plan view, schematic representation of an ASIC according to one embodiment of the present invention.

FIG. 3 shows a digital circuit 40 according to one embodiment of the present invention. Circuit 40 (also shown in FIG. 8D) is a plan view representation of an ASIC 40 according to one embodiment of the present invention. Controller 40 is adapted and configured for use as an electronic device implantable within an animal. ASIC 40 includes a pair of differential EMG inputs, each of which accepts a voltage from a corresponding electrode that is in contact with tissue of the animal. These signals are provided to an amplifier and filter section, with the amplified and filtered data signals being provided to a digital logic portion of the ASIC that applies various logical tests to the data. This portion of digital logic provides output signals to a transmitter, and further controls the operation of that transmitter. The transmitted signal is sent via the differential antenna inputs to a dipole antenna, although various embodiments of the present invention contemplate monopole antennas, and other types of antennas. Data is transmitted by the antenna 50 to a receiving station.

ASIC 40 further includes an input for receiving power from a battery or capacitor. In some embodiments, a capacitor that stores energy in the form of ions absorbed on an electrode surface (which includes devices referred to as supercapacitors), is located on a different part of the implanted device 20. Still further, power to operate various aspects of the ASIC 40, such as the transmitter, may also come from dielectric-effect capacitors, which can provide bursts of higher power (for shorter duration) than ion-absorption type capacitors. In particular, the higher power demands of the transmitter can be served by a combination of dielectric-effect and absorption-type capacitors operating in parallel.

Figure 4:
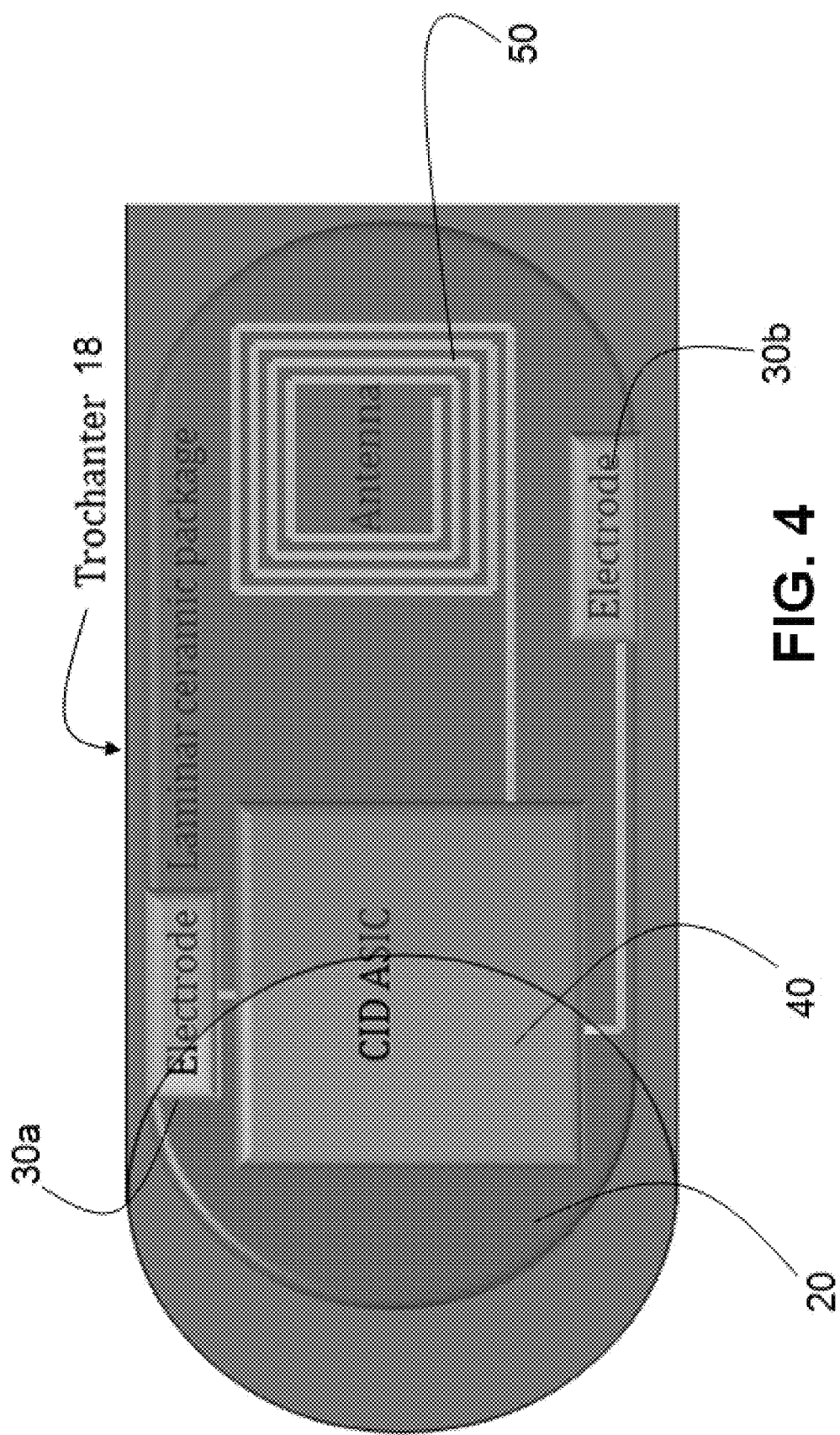
FIG. 4 is a schematic representation of an implantable EMG probe according to one embodiment of the present invention.

One form for the implant 20 is of a long narrow tubular structure as shown in FIG. 4. Implant 20 is shown schematically within a trochar 18, which can be used for purposes of implanting device 20 within an animal. FIG. 4 schematically shows that device 20 includes an ASIC 40 receiving signals for a pair of spaced apart electrodes 30a and 30b. Device 20 further includes an antenna 50 that performs the dual functions of receiving radiated Radio Frequency (RF) from an external source, and further transmits data pertaining to the animal tissue.

Figure 5:
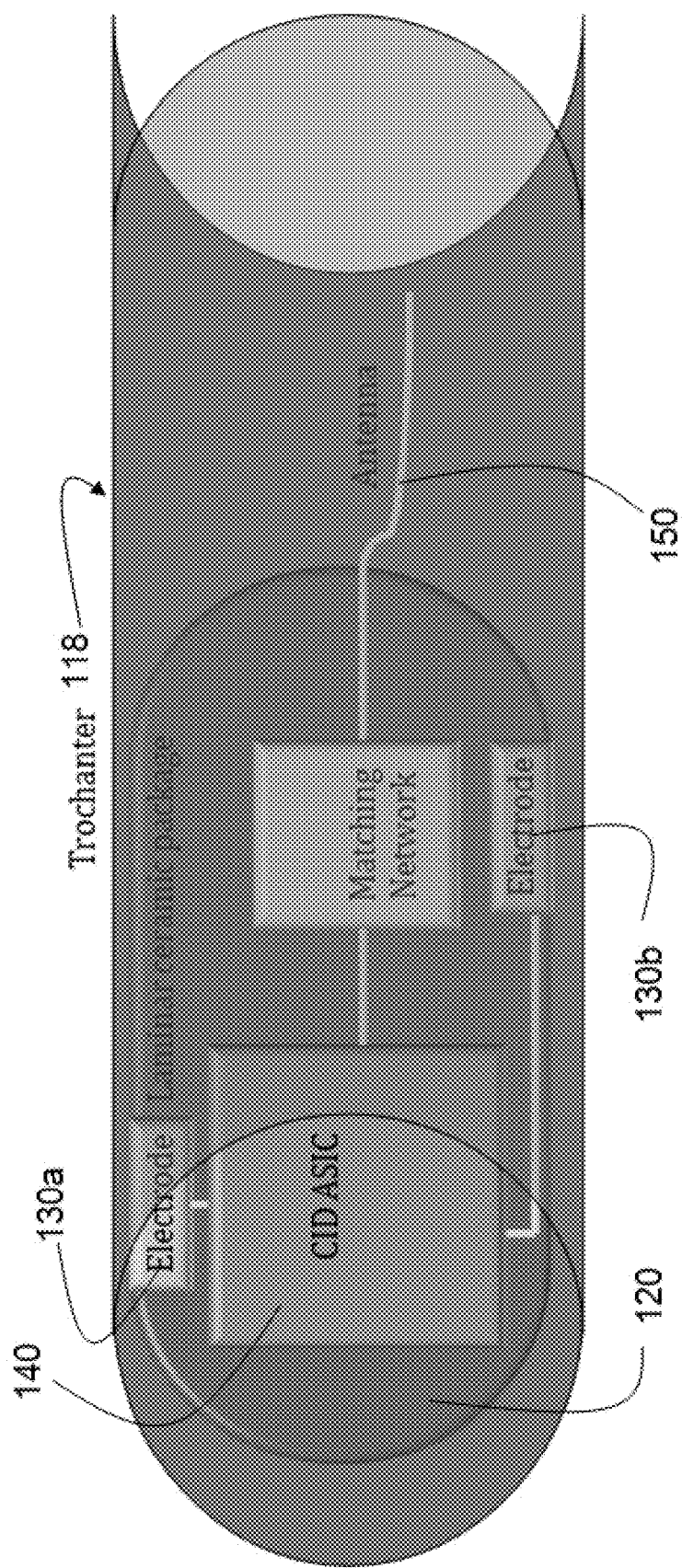
FIG. 5 is schematic representation of an implantable EMG probe according to another embodiment of the present invention.
Figure 6:
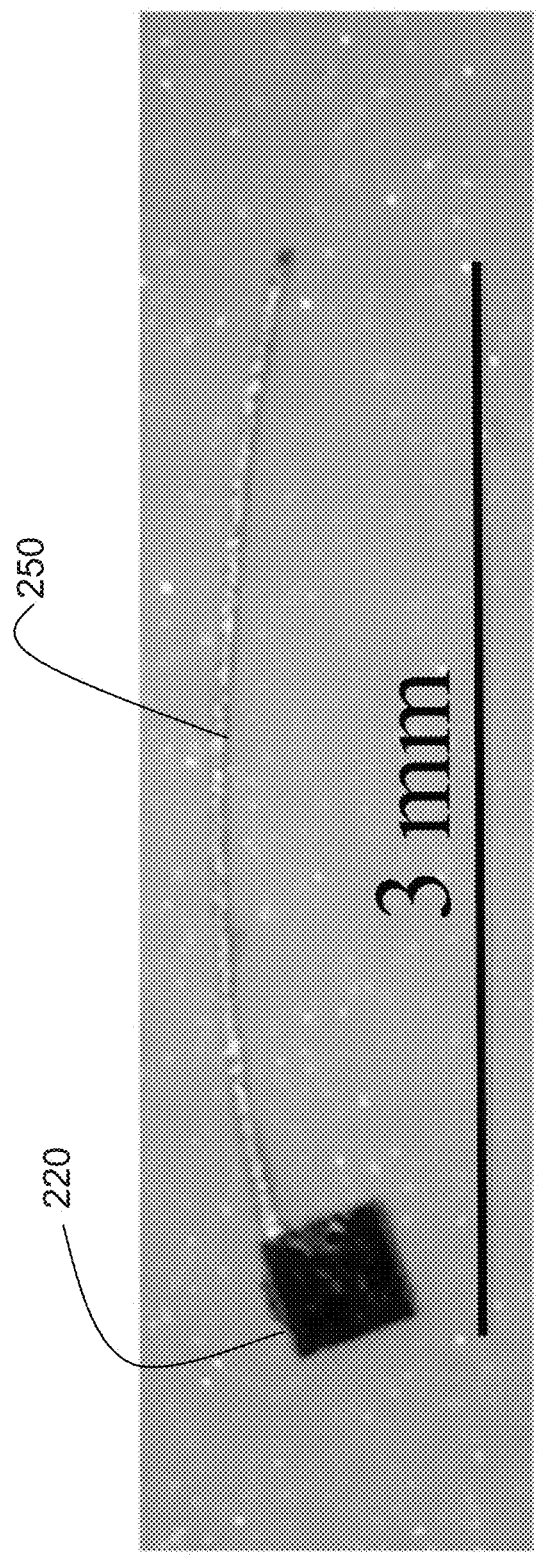
FIG. 6 is a schematic representation of an implantable EMG probe according to another embodiment of the present invention.

FIGS. 5 and 6 show yet other configurations of implantable devices. FIG. 5 shows an implantable device 120 generally the same as device 20, except including a monopole antenna 150 extending outwardly, and communicating with the ASIC 140 by a matching network. FIG. 6 shows yet another embodiment in which the implantable device 220 includes a long monopole antenna 250 extending outside of the enclosure of device 220. In some embodiments, the device shown in FIG. 6 can be used to place the active device (and its electrodes) near the desired location of animal tissue, and the antenna 250 extending outward and preferably toward the base station for improved reception of power and improved transmission of data.

For normal muscle (as with transradial amputees) the implant can have electrode poles space of about a millimeter apart. However, for TMR another embodiment has the electrodes about 10-15 mm apart so that a broader area of reinnervated muscle could be recorded from, but not so long as to be sampling from two separate muscles or so long as to cause structural issues. The electrodes 30 can also cover the ends of the implant, thus they do not need to add to the length of the implant.

Figure 8A:
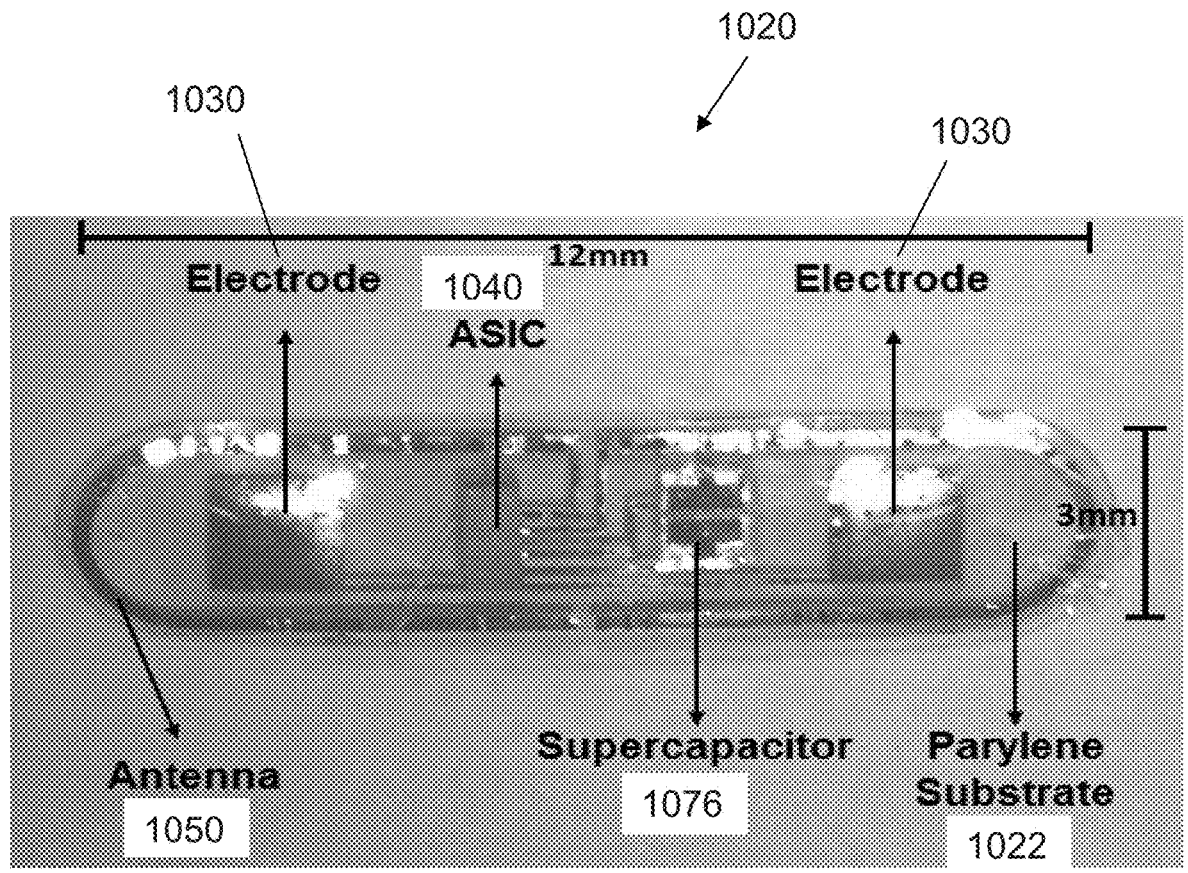
FIG. 8A is a top plan view photographic representation of an implantable device according to one embodiment of the present invention.
Figure 8D:
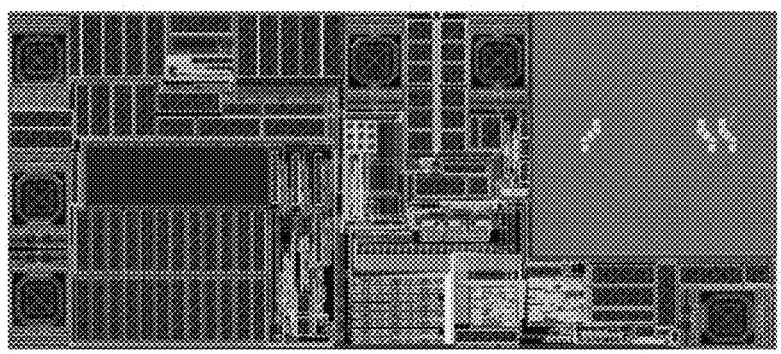
FIG. 8D is a schematic CAD representation of the photographed ASIC of FIG. 8C.
Figure 8C:
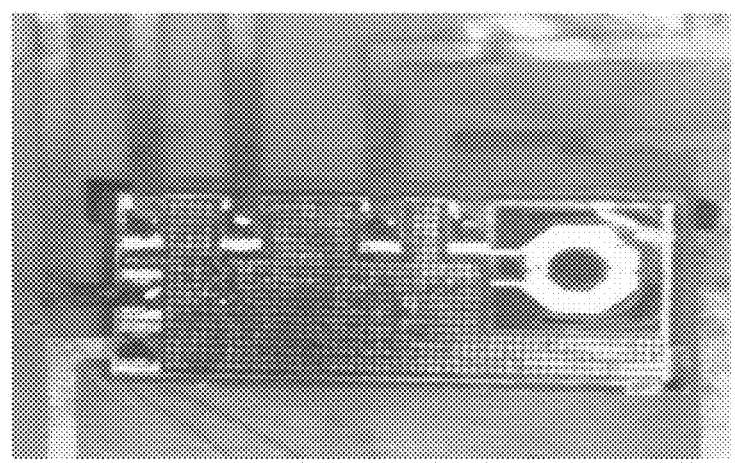
FIG. 8C is a close-up photograph of the ASIC of the device of FIG. 8B.
Figure 8B:
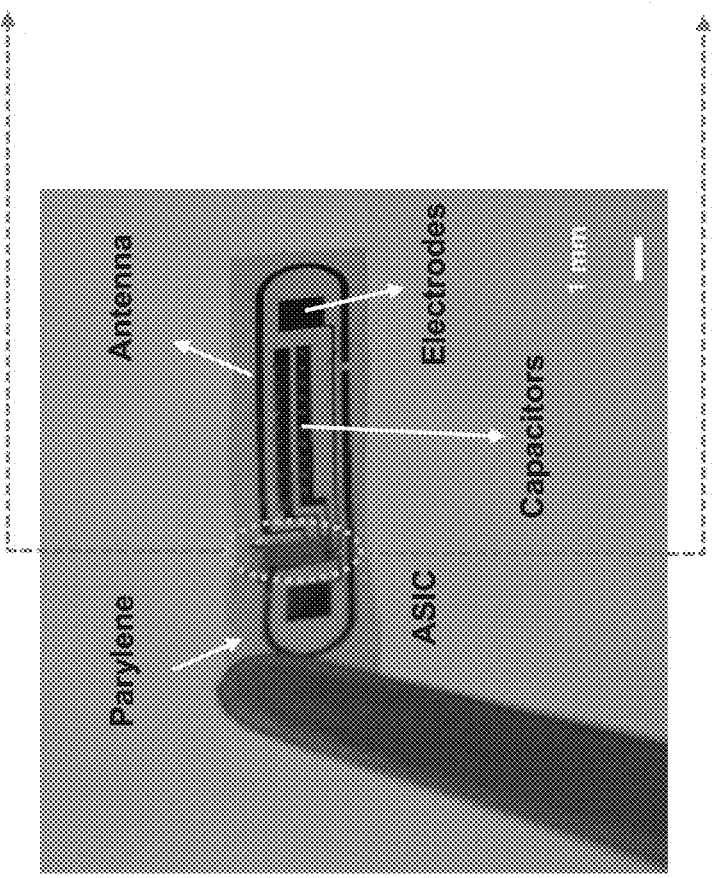
FIG. 8B is a top plan view and photographic representation of an implantable device according to another embodiment of the present invention.
Figure 8E:
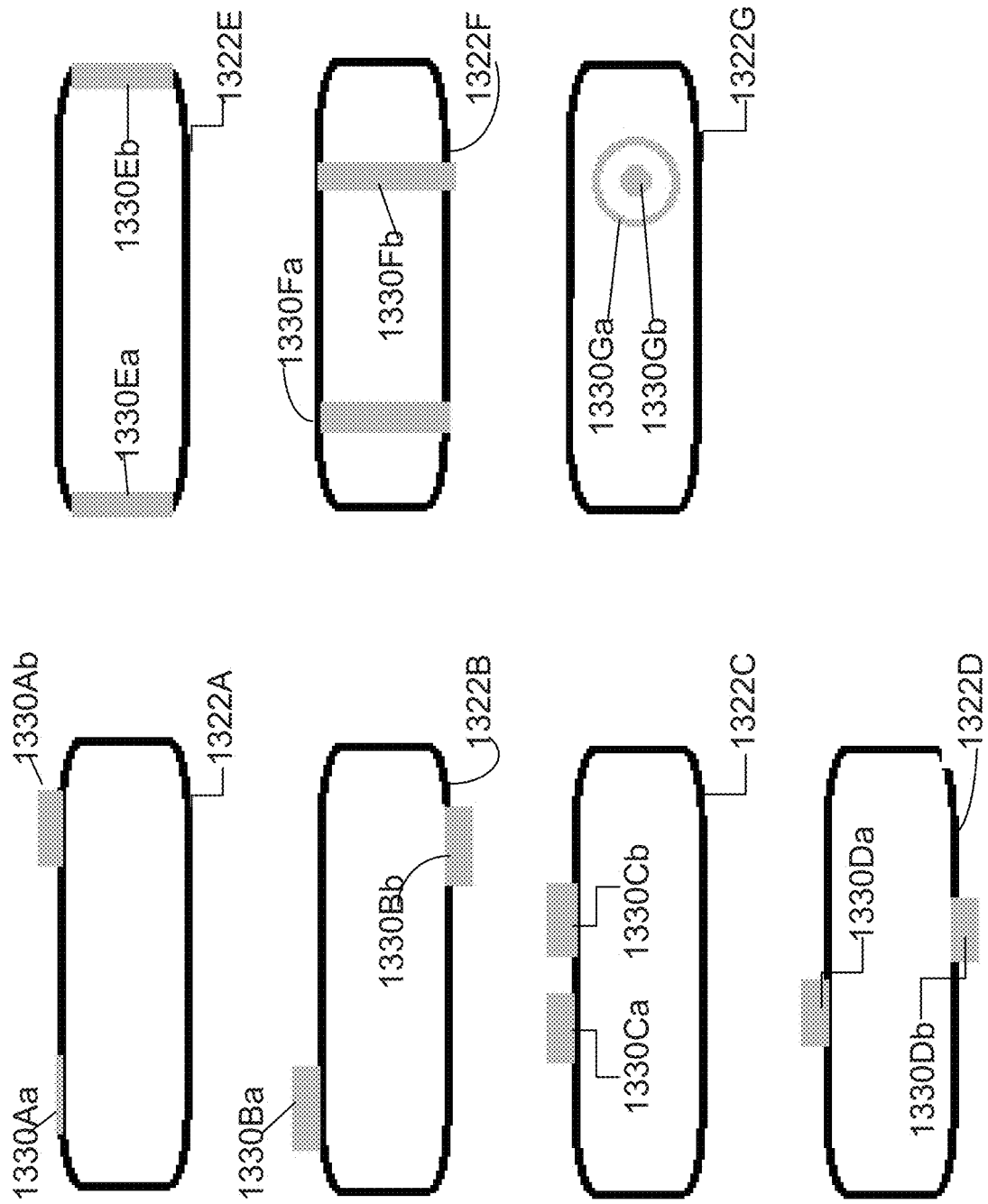
FIG. 8E shows various schematic representations of electrode configurations for an implantable device according to various embodiments of the present invention.

FIG. 8E shows a plurality of different electrode configurations according to various embodiments of the present invention. FIG. 8E shows seven different configurations of an implant substrate 1322, with the electrodes 1330a and 1330b shown schematically. Substrate 1322 is shown schematically in each of the figures as generally oblong and rounded, with a pair of longer laterally-extending opposing edges (lateral being left to right), spaced apart by a vertical width (vertical being top to bottom as shown in the figure). It is further understood that the substrate 1322 (and the corresponding implant 1320) also has a thickness dimension, which is not shown in FIG. 8E for sake of simplicity. However, it is understood that the various combinations shown in FIG. 8E also pertain to electrodes positioned more toward the top or bottom of the finished device 1320 (top to bottom being in and out of the plane of FIG. 8E).

Substrate 1322A includes electrodes 1330Aa and 1330Ab located on the same longitudinal edge, and spaced apart by more than half the overall length of the substrate. Substrate 1322B shows first and second electrodes 1330Ba and 1330Bb on opposing longitudinal edges, and spaced apart by more than about half of the overall length of the substrate. Substrate 1322C shows first and second electrodes 1330Ca and 1330Cb located along the same edge and spaced apart by an amount less than about half the overall length of the substrate.

Substrate 1322D shows first and second electrodes 1330Da and 1330Db, respectively, located on opposite longitudinal edges of substrate 1322. In some embodiments, the electrodes are laterally spaced apart less than about half the overall length of the substrate (as shown), whereas in other embodiments the electrodes are spaced apart by more than about half the overall length, and in still further embodiments the opposing electrodes are generally laterally coincident with each other.

Substrate 1322E shows first and second electrodes 1330Ea and 1330Eb, respectively, located and generally on opposing ends of substrate 1322. Substrate 1322F shows first and second electrodes 1330Fa and 1330Fb, respectively, spaced apart in a manner similar to that shown in substrates 1322A and 1322B, but extending generally across the top or bottom face of the substrate.

Substrate 1322G shows first and second electrodes 1330Ga and 1330Gb, respectively, in which one electrode extends along a curved path, and the other electrode is located generally within that curved path. In some embodiments, the first and second electrodes are arranged concentrically. In yet other embodiments it is understood that both electrodes can extend along curved pathways.

The various electrode configurations shown in FIG. 8E are applicable to a kit of implantable devices provided to a surgeon. In some embodiments, the kit includes a plurality of members, each of the members (devices) having a different configuration of electrodes. By providing such a kit, the surgeon can select the configuration of electrodes best suited to implantation in a particular tissue of the patient.

The number and location of implants that may be used varies by amputation level and from patient to patient. Generally 6-8 surface electrodes are used with both transradial pattern rec control and for TMR pattern recognition control. A similar number of implants should be adequate for an IEMG system. However, up to 16 electrodes could be used to supply higher fidelity of signals form and/or more independent signals from normal muscles.

FIGS. 1 and 10 show various embodiments of the present invention pertaining to a system of implants 20 and 1220, respectively. Referring to FIG. 10, it can be seen that a plurality of implants 1220-1 through 1220-6 are placed within the tissue of an animal. Each of these implants includes a corresponding antenna 1250-1 through 1250-6 for communication with the antenna of a base station 1211. FIG. 10B shows that each of the devices-1 through -6 transmits data to the base station in preferentially sequential, non-overlapping periods of time. During the transmitting period, a stream of data pertaining to the locally-detected tissue is broadcasted, preferably with a header and various error correction codes. In one embodiment, the system uses a BFSK modulation scheme in the 2360-2400 MHz band. In some embodiments, a 915 MHz powering signal is used to identify the currently active device. Half duplex communication is used to communicate to each implant sequentially, further using time division multiplexing with a sleep mode and an active mode. FIG. 10C shows that in some embodiments device 1 is active and broadcasting for a short period of time, and generally in a sleep mode in between. However, it is possible that during the sleep mode various measurements are being taken, but generally the transmitter (which consumes a relatively large amount of power) is turned off. It is possible that data sampled during the period of sleep is stored and saved for transmission during the active time of the implant. However, in yet other embodiments, the sleep time is relatively short, such that no substantial time resolution end data is lost by sampling only during the active periods. In still further embodiments, the data transmitted during the active time is a running average of data sampled during the sleep time.

Implants could be placed by either an open surgical technique or through an injectable form factor using a trochar. In some cases, placement during an open surgery (like TMR) might be possible and desirable. However, the device can be placed through an injectable system using a trochar. An injectable system has the advantage of minimizing surgery, enabling outpatient surgery or even office based placement. Wound size would be smaller and recovery from placement would be faster with an injectable method. It would also facilitate additional or replacement channels to be installed at any time.

Some embodiments of the implant should have the following features: the electrodes are about 5-15 mm apart placed on the exterior of the body of the implant; the electrode poles should have a cross sectional diameter of 3 mm or less (one package size; the electrodes are made of a highly conductive material that is not corroded by the human tissue environment; or the implant need not have a tubular shape, and can have any rounded shape adapted and configured for implantation via a trochar or similar medical device; however, they should not have any sharp edges that will lead to tissue irritation and inflammation. The final form is further dependent on the antenna design. Various embodiments shown herein include dipole antennas that generally wrap near the edges of the implanted device, monopole antennas that extend along the length of the device, meandering shapes (such as that shown in FIG. 9A) located within the device substrate X22.

The analog front end consists of a ultra-low-power, fully differential neural amplifier. It is capable of detecting ultra-low signals (~5 μV) with minimum input referred noise (<200 nV/Hz), achieving satisfactory signal-to-noise ratios which ease A/D converter requirements. A fixed-gain low-pass filter that serves both as an anti-aliasing filter and buffer drives the A/D converter input from the neural amplifier. The neural amplifier and filter combination is designed so that low (500-5 KHz) and high-pass (0.05-100 Hz) frequencies and mid-band gain (30 dB-50 dB) can be reconfigured wirelessly. This gives the clinician more flexibility over channel conditioning and allows for optimization of each implanted EMG unit to the specific signal observed between its electrodes.

The A/D converter used in one embodiment in the signal chain is a 10-bit charge-redistribution successive-approximation register (SAR). 10 bits is expected to be sufficient and reduces power consumption. The SAR A/D converter allows more flexibility for post-processing for different sampling rates. Some embodiments use monotonic capacitor-switching with half the number of capacitors used in a conventional architecture and consume less than 50 μW of power at 5 Ms/sec. ADC sampling frequency and resolution can be programmed. Data serialization and encoding prior to transmission is embedded in the SAR logic. The signal conditioning chain has a power-down mode that allows it to 'sleep' when not in use. In a multi-channel application channels can powered down after reading. The signal conditioning chain uses just one external resistor (for bias generation) and one capacitor. It consumes less than 200 μW peak from a 1.8V nominal supply. Various aspects of an implanted device according to one embodiment are shown in the following table, it being understood that this is provided as reference only, and not intended to be limiting.

| Block | Parameter | MIN | TYP | MAX | UNITS |
|---|---|---|---|---|---|
| Amplifier/Filter | Detectable Input Amplitude | 0.033 | | 16.8 | mV |
| | Amplifier Gain | | | 37.1 | dB |
| | Band Pass Response | 2.2 | | 1180 | Hz |
| | Input Impedance | 0.42 | | 227 | MΩ |
| | Input Referred Noise | | 9.4 | | uV |
| ADC/Clock | Output Bandwidth | −1.2 | | 1.2 | V |
| | Data Resolution | | 10 | | Bits |
| | Clock Frequency | | 250 | 300 | kHz |
| Digital Logic | Sampling Rate | | 5 | 7 | kHz |
| | Data Rate | | 50 | 70 | Kbps |

Low-power prolongs implant life and prevents localized heating. Supply voltage downscaling can be used to reduce power consumption. It is preferable to reduce the bias current while ensuring reliable operation and acceptable efficiency. This tradeoff can be addressed using current reuse: the power amplifier can be stacked on top of the voltage-controlled oscillator and can re-use the bias current while keeping the signal flow sequential, thereby cutting the power consumption in half.

For the implant transceiver, a 2.4 GHz ISM-band transmitter drives a 50Ω load, provides power, ensures data reception when implanted, and operates at low current. A voltage-controlled oscillator can be used to modulate the data using on-off or binary frequency-shift keying. A complementary cross-coupled topology can be used for on-chip implementation, low phase noise, and low power consumption. The voltage-controlled oscillator will be fed through a self-biased class AB power amplifier stacked above it. The power amplifier will be used to buffer the oscillator from a potentially varying load and to improve the transmitter output power. This is helpful, as the load presented by the implanted antenna varies unpredictably with the motion of conductive objects (e.g. arms) near the implant.

| Block | Parameter | MIN | TYP | MAX | UNITS |
|---|---|---|---|---|---|
| Transmitter | Transmitting Frequency | | 2.46 | | GHz |
| | Average[1] Transmitter Output Power | | 1.26 | | μW |
| | Peak Power Consumption | | 1.04 | 1.26 | mW |
| | Output Impedance | | 50 | | Ω |

[1]Equal to peak transmitter power multiplied by expected duty cycle to reflect power savings from burst transmission.

Due to the high data transfer rate of the RF system, the transmitter for a device in some embodiments operates intermittently. Sampling at 1 kHz/10 bits results in 20 kbs data rate per implant, such that 0.125% of the implants' transmitting capacity is used, limiting average power consumption per implant to <625 nW. Signal conditioning can include variable filtering, variable amplification, and 10-bit ND with an estimated average power consumption of 200 nW when turned off between sample acquisitions. The total power per implant can be under 1 μW.

One factor for the external transmitter power is the depth of implantation. There is an RF power transfer efficiency of 0.1% in air at 1 m (i.e. 1 mW avg. to receive 1 μW). The power need multiplies by ~10-1,000 as the implant is placed deeper in the tissue: 0.01-1 W of average power is needed for depths of 0.1-5 cm.

In order to facilitate a reliable working device the power consumption of the implanted device should to be as low as possible, so as to reduce the amount of power (a) dissipated into the tissue (biocompatibility) by the device during outward-bound data telemetry and (b) used to be delivered into the tissue to provide wireless power to turn on and operate the device. Each implantable EMG unit has a power consumption associated with each of its main electronic sub-blocks: the transmitter, and the signal conditioning. The power management sub-block's power consumption is built into the efficiency of that unit. In its current implementation, the transmitter has a measured peak (worst case) power consumption of 500 μW. It transmits at a rate of 8 mbps. In one embodiment each EMG unit samples with a resolution of 10 bits per sample, and at a rate of 1 kHz. That translates into a data-rate of 10 kbps per implant. Therefore, the transmitter needs to be on 0.125 percent of the time. Note that the transmitter does not turn on and off for each sample, and instead can acquire a series of samples (e.g. 1,000 or 10,000) and then transmit them all together.

Another sub-block is the signal conditioning unit (i.e. amplifier, filter, ND, and signal processing algorithm if any). One embodiment utilizes a near sub-threshold neural amplifier coupled with high and low-pass filtering and a successive approximation register (SAR) analog-to-digital converter (ADC). The measured continuous power consumption for this approach is 100 μW. Powering down between sample acquisitions helps dramatically reduce the power consumption. The amount of time to power up, acquire, and store a sample is on the order of 10 μs in one case.

In some embodiments, the signal is sampled at 1 kHz, the signal conditioning block is on for 1% of the total time, and the average power consumption for this unit is 1 μW. Assuming an RF powering efficiency of about 0.1%, uses an external power source at 1.7 mW average power. As the implant goes deeper into the body this gets ~10-1,000 times worse with tissue attenuation. The external device can generate 17 mW-1.7 W of average power to power an implant depending on depths from 1 mm-5 cm. Alternatively, yet another embodiment floats an antenna to the surface (Type 2 implant as described below) to get closer to 17 mW number for all cases.

| Block | Parameter | MIN | TYP | MAX | UNITS |
|---|---|---|---|---|---|
| Rectifier | Rectifier Input Power | 5.01 | | 10 | mW |
| | Rectifier Efficiency | 10 | | 20 | % |
| Voltage Regulator | Regulated Voltage | 1.71 | 1.80 | 1.89 | V |
| Whole System | Supply Current | 150 | | 700 | uA |
| | Power Consumption | | 670 | | μW |
| | Output Resolution | | 101 | | uV |
| | Stabilization Time After Startup | | 300 | | ms |
| | Peak RF Amplifier Power | 1 | | 10 | W |
| | Footprint | | 1.25 × 0.55 | | mm |

Figure 7A:
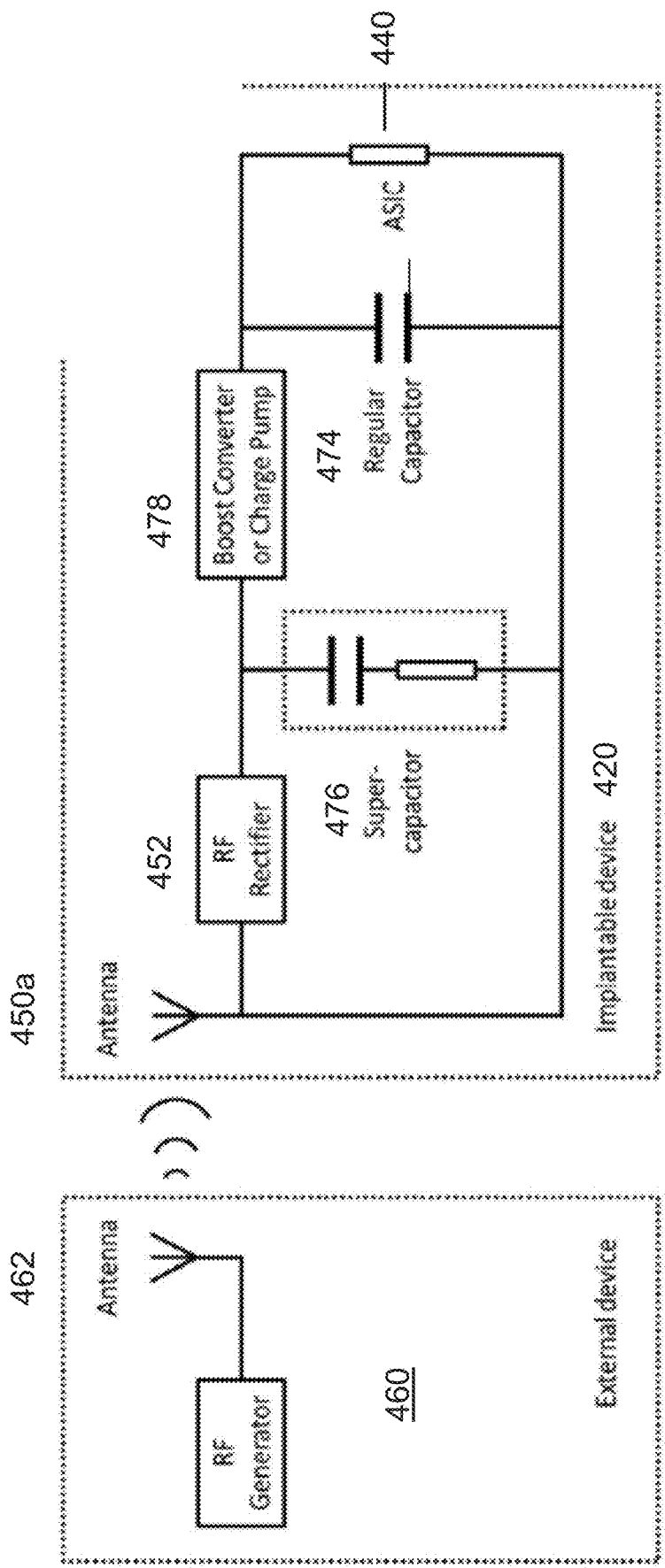
FIG. 7A is a block diagram of a power generation and storage system according to one embodiment of the present invention.
Figure 7B:
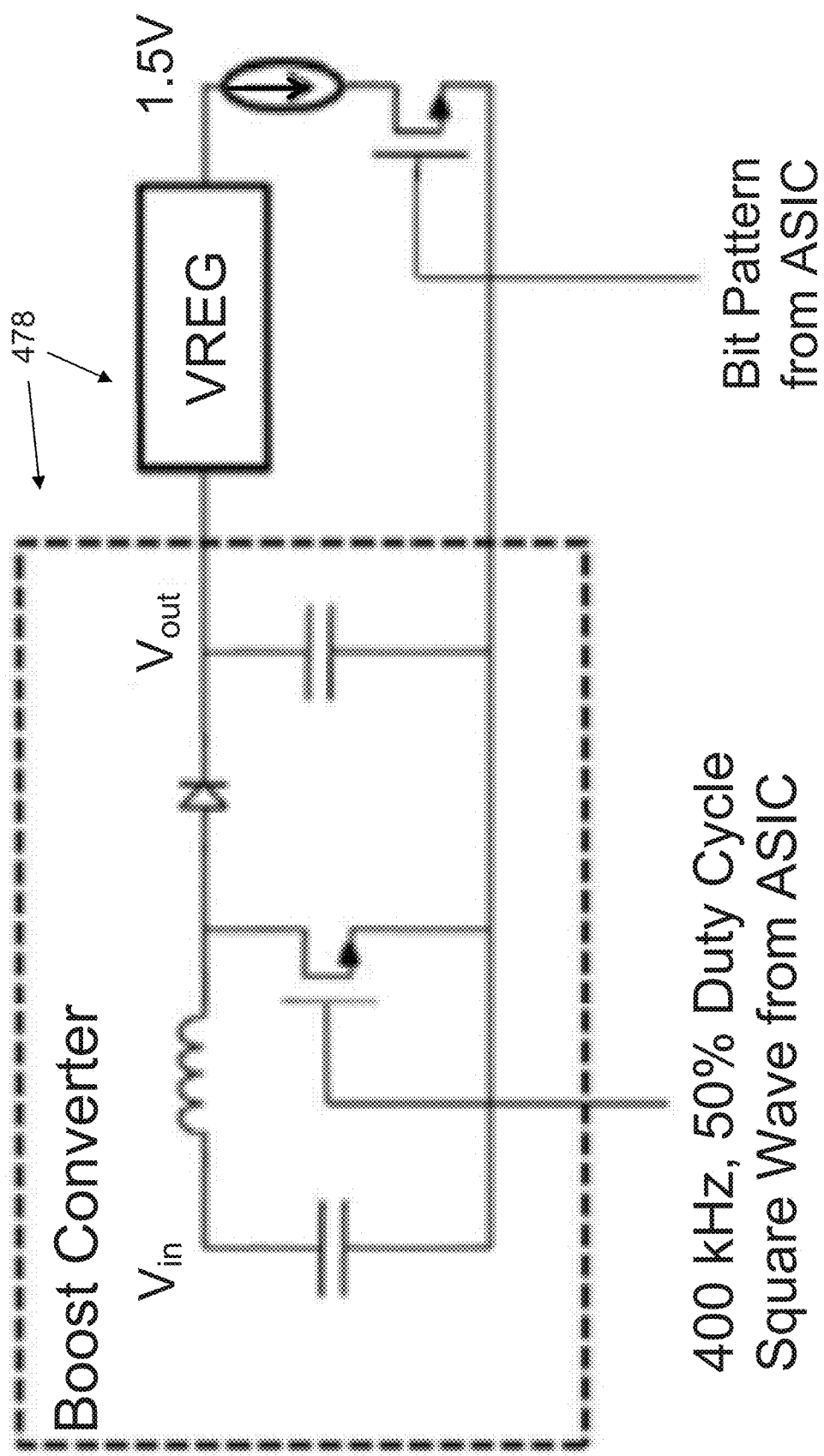
FIG. 7B is a block diagram of a circuit according to another embodiment of the present invention.

FIGS. 7A, 7B, and 8A show various embodiments of the present invention pertaining to biologically implantable devices including supercapacitors. FIG. 7A shows a portion of an electrical schematic diagram for an implantable device 420. It can be seen that power generated by an external device 460 is broadcast by an antenna 462 to any of a plurality of power-receiving antennas 450a, each implantable device 420 having at least one antenna. As noted previously, in some devices a single antenna provides both a power receiving capability and also a signal transmitting capability, whereas in other embodiments the two functions are provided by the same antenna.

Implantable device 420 includes an RF rectifier 452 that receives power from antenna 450a, and provides a rectified voltage to an input of an ion absorption-type capacitor 476, such as a supercapacitor. Such devices are characterized by relatively high specific energy (higher than the specific energy of dielectric-effect capacitors), but lower specific power (lower than the specific power of dielectric-effect capacitors). The ratio of specific energy to specific power has units of time, and supercapacitors typically have such time constants that are about 100 to 1000 times longer than the time constant of dielectric-effect capacitors (such data often being shown as a Ragone plot).

The second capacitor 474 exhibits different and complimentary characteristics to the first capacitor 476. The first capacitor 476 stores a relatively larger charge but with a higher internal series resistance (making it an inefficient source). The second capacitor 474 stores a relatively less energy but with lower internal series resistance. The first charges the second slowly (i.e efficiently). The second can supply the rest of the system.

Various embodiments of the present invention provide for power storage that recognizes the ability of a supercapacitor to store relatively large amounts of energy, and the ability of regular capacitors to provide high levels of power. As discussed above, one of the higher power consumption items in an implantable device described herein is the transmitter. The logic and topology of the ASIC disclosed herein operate the implantable device X20 such that the transmitter is on for short periods of time. However, the base station is radiating power over longer periods of time, and in some embodiments providing this radiated power constantly. Therefore, in one embodiment, the power storage of the implanted device includes a combination of high absorption type and dielectric effect capacitors. The supercapacitors provide for storage of the radiated power, and a regular capacitor provides for the relatively short bursts of high power needed by the transmitter. As best seen in FIG. 7A, the supercapacitor 476 and regular capacitor 474 are shown in parallel with each other, and preferably in parallel with ASIC 440. In some embodiments, a boost converter or charge pump 478 provides an interface between input terminals of capacitors 476 and 474.

It is understood that in paragraphs to follow various specific aspects of one or more embodiments of an implantable device will be discussed, but that such discussion is by way of example only, and not to be construed as limiting.

The external electronics will receive data from the internal unit, perform any data conditioning, and prepare the data for transmission to the prosthesis controller via a CAN bus. It includes a power regulation circuit and a microcontroller or similar programmable logic device for controlling its operations. The implant controller will be designed to fit into a prosthetic limb.

Down-conversion. The first stage of down-conversion is a Maxim IC (MAX2644) low-noise amplifier (LNA). This serves to lower the noise figure of the receiver down-conversion chain and preferably provide a better than 17 dB gain. The second stage of down-conversion is mixing the output from the LNA with 2.38 GHz. A Maxim IC (MAX2750) voltage-controlled oscillator generates the 2.38 GHz frequency. The voltage-controlled oscillator output, at −3 dBm, is fed into a Maxim IC (MAX2680) low intermediate frequency (IF) mixer which down-mixes 2.5 GHz to 120 MHz and 2.4 GHz to 20 MHz. The mixer IF output is fed into a Maxim IC (MAX2650) low-noise amplifier, optimized for lower frequency ranges providing low-noise as well as a 20 dB gain.

Amplification and Filtering. After IF amplification the signal is filtered through a 3rd order T network bandpass filter. The center frequency is at 120 MHz with a 20 MHz bandwidth. The filter serves to preserve the 120 MHz signal and eliminate the higher IF mixed signals as well as the 20 MHz corresponding low IF signal. After filtering the 120 MHz IF signal, a second Maxim IC (MAX2650) low-noise amplifier is used to provide an additional 20 dB of gain. A 500 MHz low-pass filter eliminates the strong LO signal prior to amplitude detection.

RF Amplitude Detection and Digitizing. The isolated 120 MHz signal is fed into a Linear Technology RF power detector (LT5538). The RF power detector has sensitivity down to 75 dB and serves to demodulate the isolated 120 MHz on-off keying signal. The RF power detector outputs a square-wave corresponding to a digital signal. A digital signal with 3V high and 0 V low is obtained through the use of a Linear Technology High-speed Comparator (LT1719).

CAN Interface. The data output from the receiver is a digital stream (high=3V, low=0V) and interfaced with a Freescale HCS12 microcontroller. The microcontroller performs integrity checking on the received data, coordinates data collection among implants, and reports recorded data to the Master Controller via CAN bus.

Figure 9A:
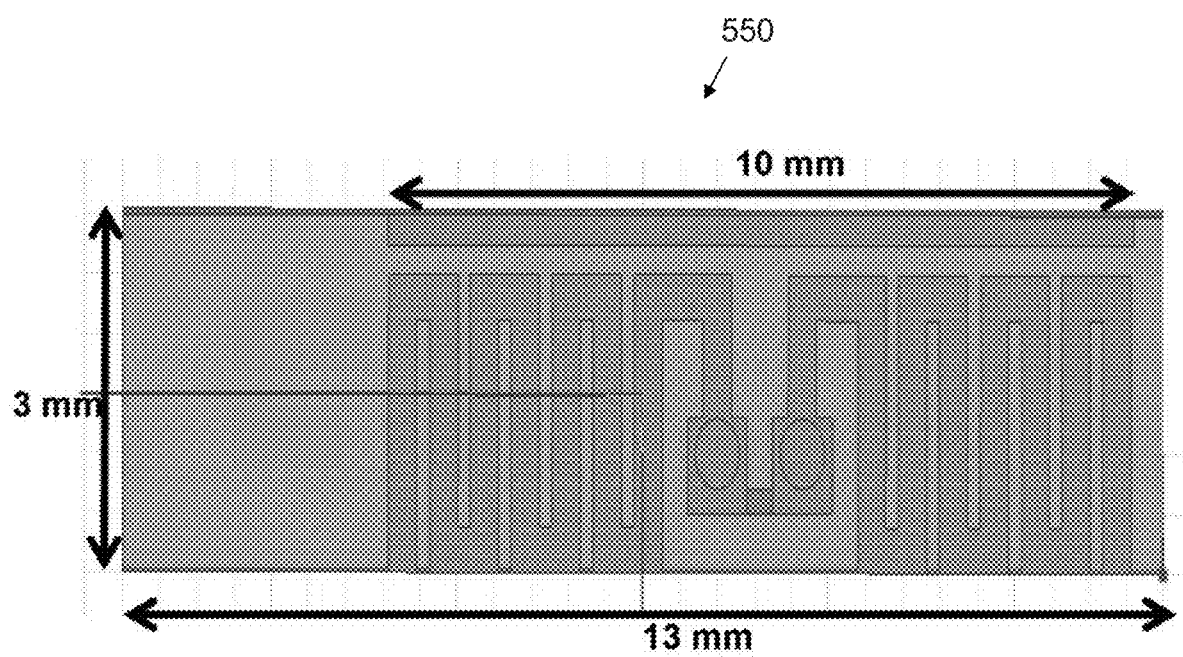
FIG. 9A is a schematic representation of a planar view of an antenna according to one embodiment of the present invention.
Figure 9B:
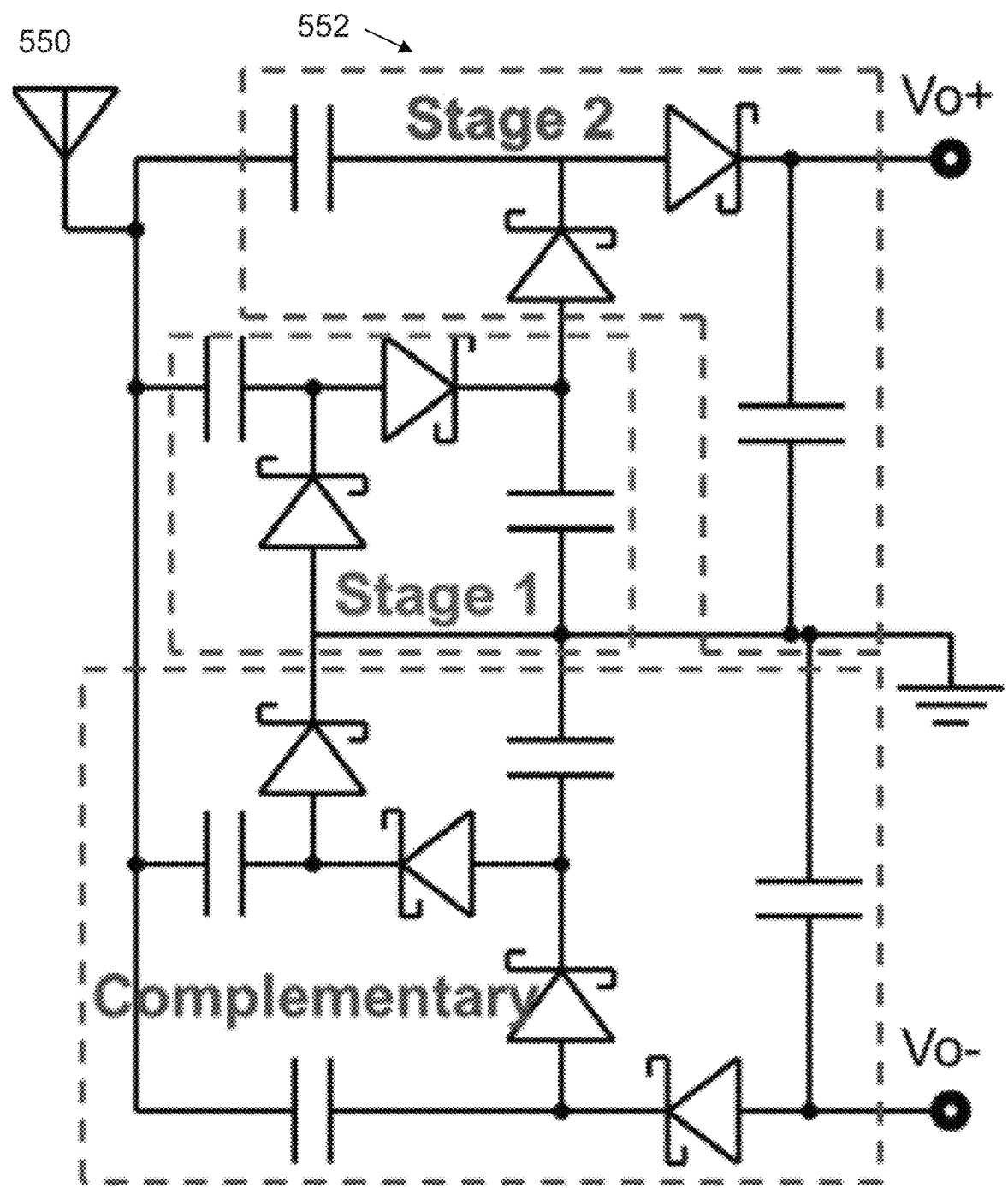
FIG. 9B shows an electrical schematic circuit of a rectifier for the antenna of FIG. 9A.

Wireless Power Delivery. Coupling power via RF electric fields propagating between broad-beam external antenna and internal antenna 50 allows greater freedom of placement, greater operating distance and better misalignment immunity than inductive power coupling. One such antenna 550 is shown schematically in FIG. 9A. The 2.4 GHz ISM band allows for a smaller antenna than lower bands, without the high tissue losses seen at higher frequencies. The 2.4 GHz frequency is available for medical products in all countries. A received RF signal is converted to dc power by an implanted device through a high-frequency rectifier circuit. A modified Cockcroft-Walton multiplier has been demonstrated to yield sufficiently high voltages with relatively low input power levels compared to PMOS voltage multiplier, full-wave diode rectifier, and gate cross-connected bridge rectifier. A converting circuit according to one embodiment of the present invention is shown in FIG. 9B. FIG. 9A schematically represents a meandering dipole antenna 550. In one embodiment, this antenna has a gain of about −11.6 dBi with the rectifier circuit of FIG. 9B having an efficiency at 2.4 GHz of about 8-9%, and an efficiency at 900 MHz of about 17-18%.

Measurements confirm that higher instantaneous power result in exponentially higher efficiencies, due to the biasing of rectifier diodes into their nonlinear region of operation. Pulsing of the RF powering wave operate the rectifier at higher efficiencies while maintaining low average powers.

Safety concerns are addressed through FDA guidelines with regards to Maximum Permissible Exposure (MPE), whole-body average Specific Absorption Rate (SAR), and spatial peak SAR Averaged Over 1 g of tissue. The following table summarizes maximum Effective Isotropically Radiated Power (EIRP) from the external powering antenna to satisfy the three FCC guidelines for safe controlled and uncontrolled radiation exposure:

| | FCC REGULATION | | |
|---|---|---|---|
| | MPE | Peak SAR for 1 g | Whole-Body Average SAR |
| Uncontrolled Exposure | 1 W EIRP at 8.92 cm | 1 W EIRP at 6.69 | 3.8 W Antenna Input Power |
| Controlled Exposure | 1 W EIRP at 3.99 cm | 1 W EIRP at 2.99 cm | 18 W Antenna Input Power |

A maximum antenna input power is given for whole-body SAR whereas a maximum EIRP and its corresponding antenna-body separation are given for MPE and peak SAR. This is because surface exposure and peak absorption rate will depend on both the radiated power in the direction of the tissue and the distance the tissue is from the source of the radiation. A general inference that can be drawn from the above table is that continuous powering at 1 W EIRP should be safe as long as the source is 8.92 cm away. Moving the external source closer to the body, as in the case of trans-humeral and trans-radial amputees, will require lowering the external radiated power. This will save power in the prosthesis battery, and reduce free-space losses. The latter partially compensates for the reduced amount of power available to the implant.

Power flux density and corresponding power available to the implant's IC under conservative conditions established by the theoretical analysis and extreme conditions that reach the MPE safety limit of 10 W/m$^2$, can be calculated from this maximum EIRP. Usable power values account for reasonable losses from antenna, matching network, and rectifier.

| Implant Location | Power Flux Density at Implant for Conservative/Extreme Conditions (W/m$^2$) | Usable Power Received by Device for Conservative/Extreme Conditions (μW) |
|---|---|---|
| Between skin and adipose | 3.20/4.41 | 7.96/11.0 |
| Between adipose and muscle | 2.62/3.61 | 6.52/8.98 |
| 1 cm into muscle | 0.844/1.16 | 2.10/2.88 |
| 2 cm into muscle | 0.222/0.305 | 0.552/0.758 |

Figure 11:
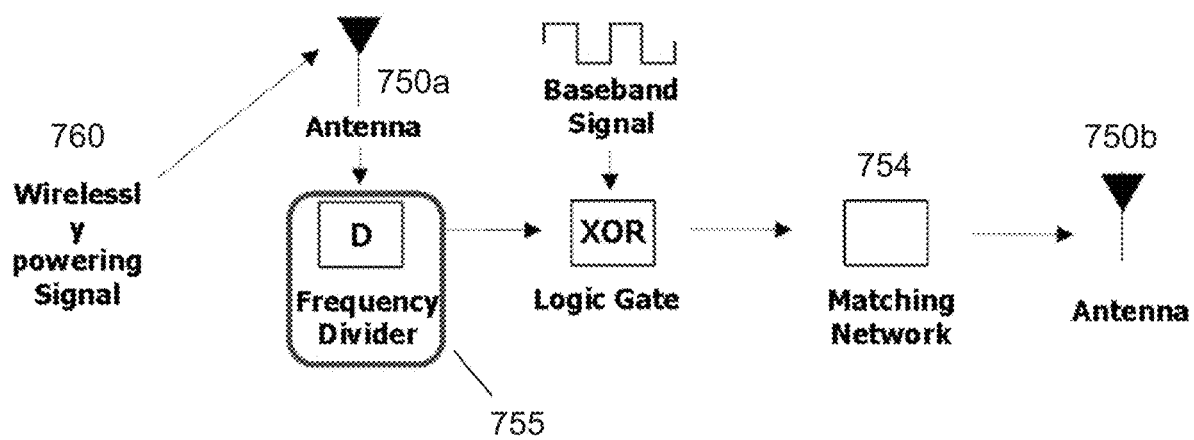
FIG. 11 is a block diagram representation of a semi-passive transmitter according to one embodiment of the present invention.

FIG. 11 is a block diagram representation of a portion of an implantable device 720 for receiving power and transmitting data. In some embodiments, there is a transmitter configuration that does not need a local oscillator to prepare a transmittable signal. Referring to FIG. 11, it can be seen that the signal from antenna 750A can be used as an input to a frequency divider, such as a D flip-flop. The output of this frequency divider is one of two inputs to an Exclusive OR Gate, the other input being the base band signal that includes tissue data. The XOR then provides an output to a matching network 754 for transmission of the data via antenna 750b.

The rectifier efficiency, implant antenna design, and optimized ASIC logic according to one embodiment that controls implant duty cycle will work towards enabling increasing depths of implantation. Additionally, lowering the RF powering frequency can, if necessary mitigate the overall risk by dramatically improving the power coupling efficiency as summarized in this table for various industrial, scientific and medical (ISM) frequency bands:

| Frequency (MHz) | Max. Instantaneous Power Flux Density (W/m$^2$) |
|---|---|
| 6.78 | 128.9 |
| 40.68 | 57.87 |
| 433.05 | 24.75 |
| 915 | 20.67 |
| 2400 | 17.79 |
| 5800 | 16.73 |

One potential concern for RF powering of devices implanted in the body is the antenna-body separation (nearly 9 cm when antenna EIRP is 1 W). However, the powering antenna can be moved closer to the skin if the input power or gain of the antenna is adequately reduced. Depending on the radiation pattern of the antenna, moving the antenna X50 closer to the tissue may focus the radiated energy such that there will be a smaller tissue volume in which a circuit can receive adequate power. In the event that multiple devices are implanted into a muscle, it may be best to use a powering antenna with a wide main beam so that a larger volume of tissue may receive similar power levels without exceeding the power flux density limits.

External Signal Processing

The implant will transmit the sampled EMG signals to a receiver module. The receiver detects and manages data transmission errors to maintain seamless temporal data in each channel. The receiver module will be capable of determining which implant each packet of data was transmitted from and will place received data on a CAN bus. An open protocol, the Standardized Communication Interface for Prosthetics (SCIP) will be used such that the received data will be compatible with additional hardware developed by third-party manufacturers.

Implant Package

In one embodiment, the implant X20 package size about is 3×15 mm (max OD) ceramic or parylene substance with poles (electrodes 30) at each end. The package has 2 ports for the electrodes of a surface area of 1 mm^2 and with an inter-electrode spacing of 10-15 mm. The implant can have an ID of about 2×14 mm (minimum anticipated ID of 1×10 mm) parylene package with antenna 50, ASIC 40, and super capacitor. Packaging material should be EM transparent (e.g. ceramic) or parylene. Wall thickness is established by expected peak and average mechanical loads using finite element analysis after the ID and length requirements are established. Package materials and fabrication should be sensitive to MRI compatibility.

Various embodiments of the present invention pertain to a plurality of devices or modules X20 that are used within a system. Individual implant modules 20 can be identified by a unique serial number that can be associated with travelers and test data developed during manufacture. This serial number can be marked prominently on the sterile packaging and the clinicians should be instructed to refer to it in all paper and electronic records regarding use of the module in a patient. Each implant module 20 can have a functional address so that any control parameters can be transmitted to it and so that data from it can be correctly assigned to its channel by the external controller.

The implanted module should be easy to implant using a tool 22 that can be provided with the system. The insertion tool 22 should minimize tissue trauma and ensure accurate percutaneous insertion. The insertion tool 22 should be designed in such a way that the location of the implant module in the desired functional region can be confirmed before the module is released into the tissue. One aspect of the implant module X20 is its ability to be implanted quickly in an appropriate position, at a maximum depth of 5 cm. Implantation tools should be designed so that the use of the tool requires less than one hour training time. The tool should be designed so that it can be inserted into tissue and used to release the device efficiently after the functional region has been identified by EMG recording or by muscle stimulation. It should be possible to perform routine diagnostic MR imaging on patients with implanted modules. During such procedures, implants will be unpowered and passive; no external equipment will be used in or near the MR magnet. Modules should be visible using fluoroscopic and ultrasound imaging to facilitate retrieval if necessary. Modules should be retrievable using minor conventional or laparoscopic surgery techniques on an outpatient basis. It should be possible to implant and operate a new module adjacent to a previously implanted module, whether the previous module is still functioning or failed, as long as the new module has a different address.

One embodiment of the present embodiment includes a fully differential single channel wireless EMG recording application specific integrated circuit (ASIC 40). In one embodiment, the chip was fabricated on a XFAB 180 nm CMOS process. The chip is capable of transmitting raw data sampled at 5 kHz and burns around 670 µW from a 1.8V supply.

In one embodiment ASIC 140 includes: single channel differential recording; passive, single-pole filters create band-pass response from 2.2 Hz-1.18 kHz; signal Gain of 37.1 dB; low power OOK transmitter operating at approximately 2.4 GHz; extremely low power (average <700 µW); and compact footprint (1.25 mm×0.55 mm). Various specific aspects of an ASIC are provided in the following table, it being understood that these specifics are by way of example only, and not to be construed as limiting.

| Block | Parameter | MIN | TYP | MAX | UNITS |
|---|---|---|---|---|---|
| Amplifier/Filter | Detectable Input Amplitude | 0.033 | | 16.8 | mV |
| | Amplifier Gain | | | 37.1 | dB |
| | Band Pass Response | 2.2 | | 1180 | Hz |
| | Input Impedance[1] | 0.42 | | 227 | MΩ |
| | Input Referred Noise[2] | | 9.4 | | uV |
| ADC/Clock | Output Bandwidth | −1.2 | | 1.2 | V |
| | Data Resolution | | 10 | | Bits |
| | Clock Frequency | | 250 | 300 | kHz |
| Digital Logic | Sampling Rate | | 5 | 7 | kHz |
| | Data Rate | | 50 | 70 | Kbps |
| Rectifier | Rectifier Input Power | 5.01 | | 10 | mW |
| | Rectifier Efficiency | 10 | | 20 | % |

-continued

| Block | Parameter | MIN | TYP | MAX | UNITS |
|---|---|---|---|---|---|
| Transmitter | Transmitting Frequency | | 2.46 | | GHz |
| | Transmitter Output Power | | 1.26 | | µW |
| | Peak Power Consumption | | 1.04 | 1.26 | mW |
| | Output Impedance[3] | | 50 | | Ω |
| Voltage Regulator | Regulated Voltage | 1.71 | 1.80 | 1.89 | V |
| Whole System | Supply Current | 150 | | 700 | uA |
| | Power Consumption | | 670 | | µW |
| | Output Resolution | | 101 | | uV |
| | Stabilization Time After Startup | | 300 | | ms |
| | Peak RF Amplifier Power[4] | 1 | | 10 | W |
| | Footprint | | 1.25 × 0.55 | | mm |

[1]Evaluated at the band-pass cutoffs (2.2 Hz and 1.18 kHz)
[2]Measured over the band 2 Hz to 2 kHz
[3]Depends on physical properties of selected antenna design.
[4]Duty cycle will vary from 10-100% to ensure average power is always ≤1 W.

Figure 12:
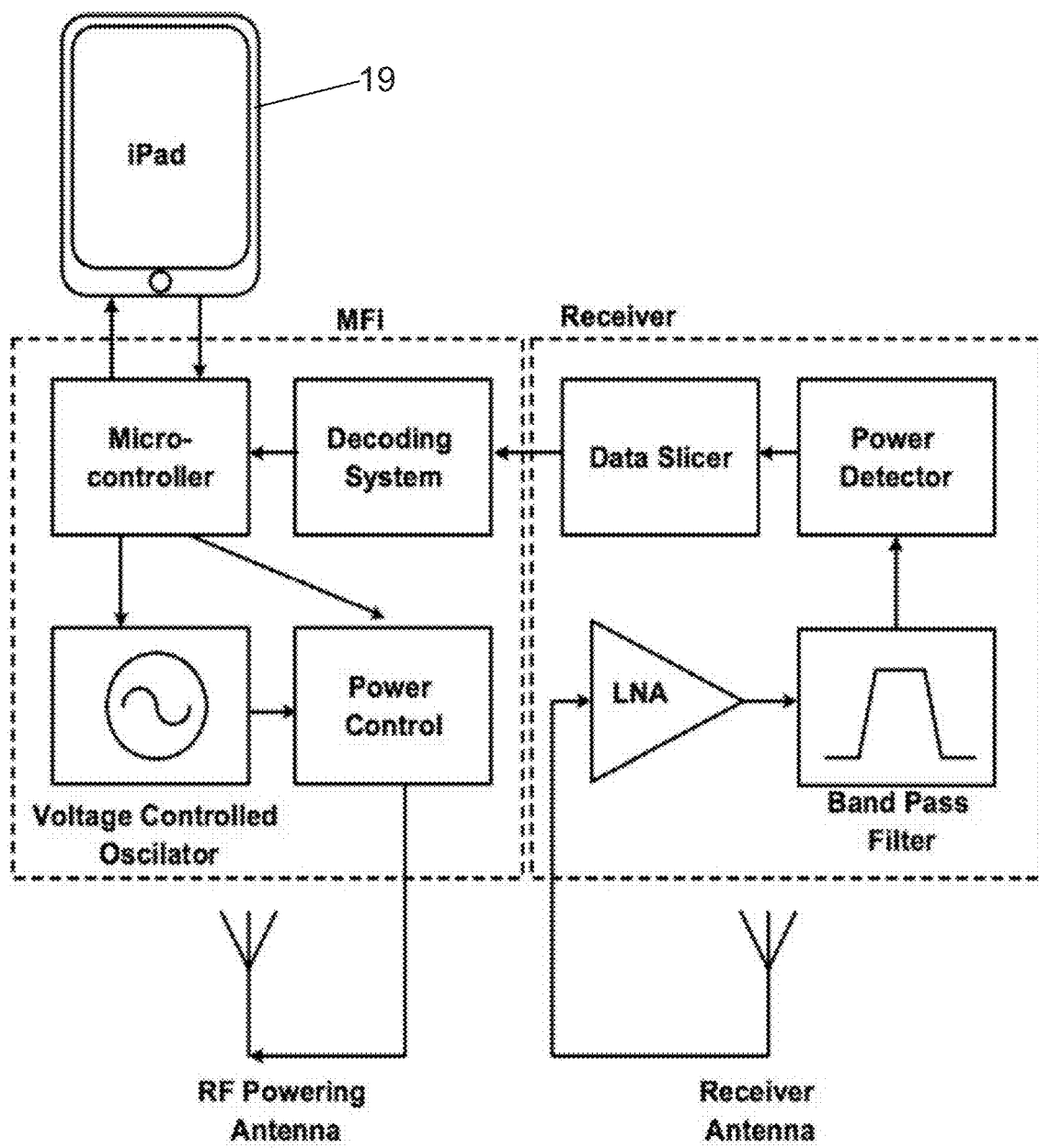
FIG. 12 is a block diagram of an external interface according to one embodiment of the present invention.

Preferably the ADC works at a fixed rate of around 20 k samples per second. The digital logic retrieves the values provided by the ADC every 200 µs (sampling at 5 kHz) and does a parallel to serial conversion. The transmission of each bit is broken down into 2 us of bit-transmission and 8us of off time for the cap to get charged up. A transmission has also a start pattern and a stop pattern attached to it. The pattern was chosen to logic high for both the start and the stop so that it helps in both data recognition and also for the receiver to match the transmitter frequency FIG. 12 is a block diagram of a system for receiving transmission from an implanted device X20, demodulating the transmitted data, and visualizing the data in real time on a portable device.

Figure 13:
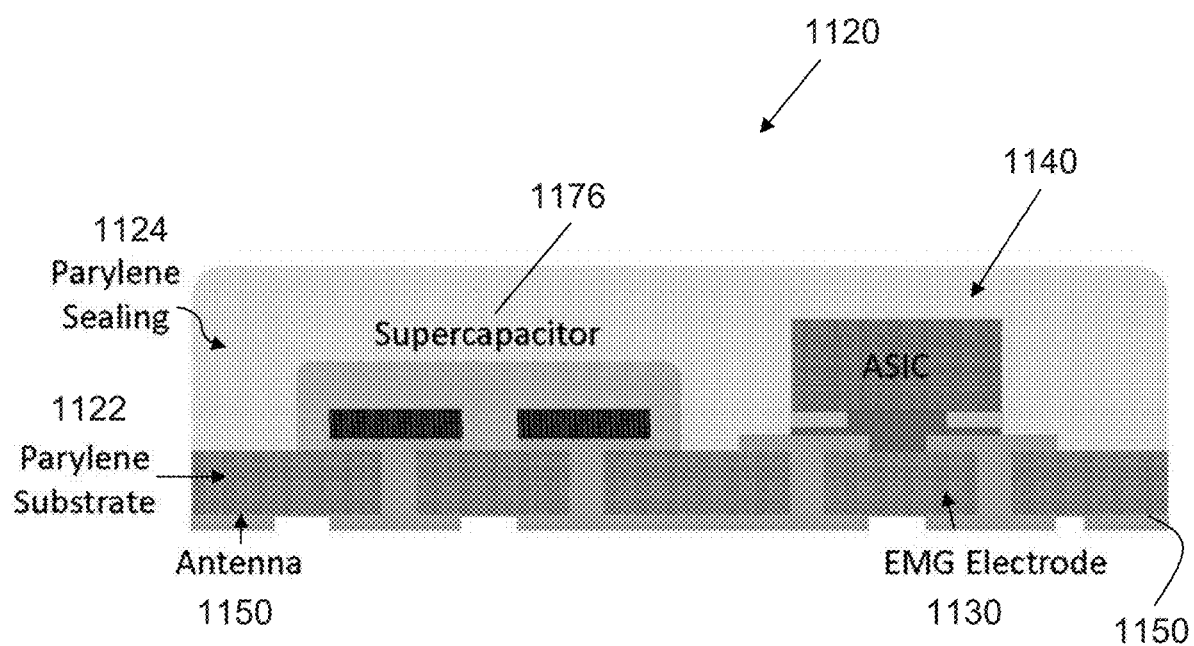
FIG. 13 is a schematic, cross-sectional representation of an implantable device according to one embodiment of the present invention.
Figure 14:
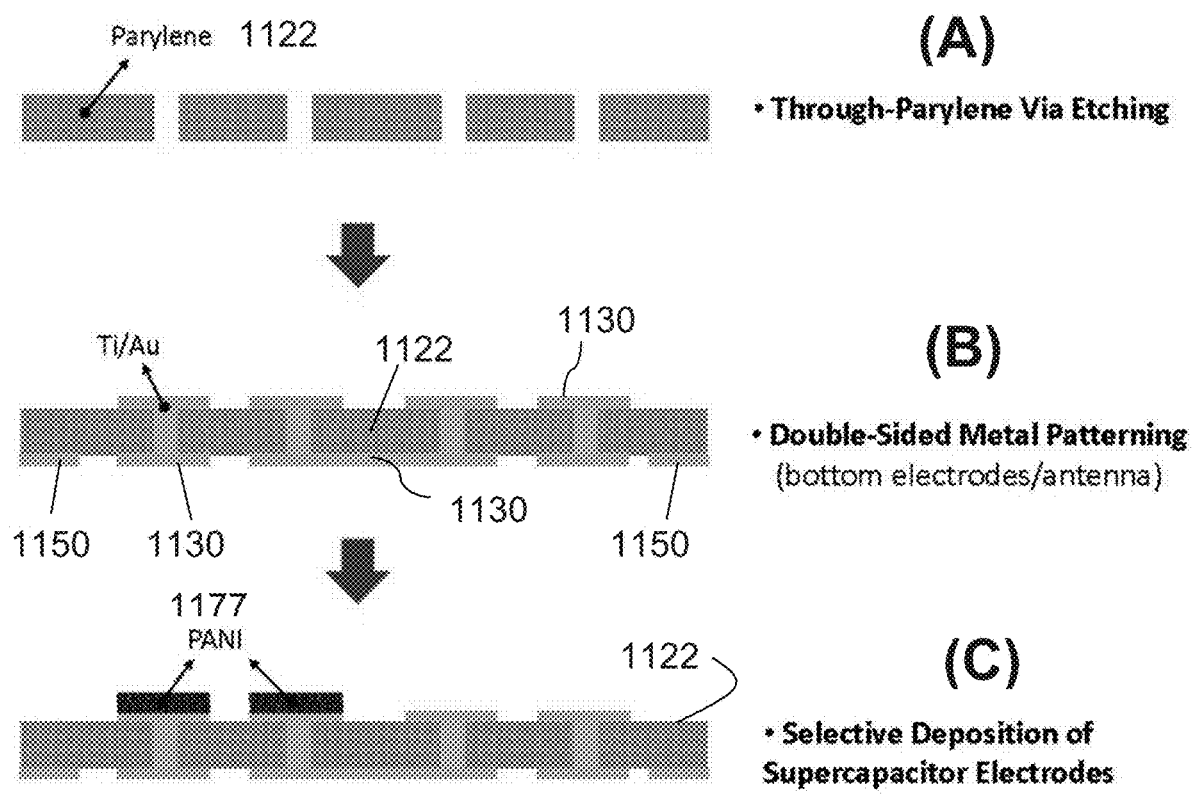
FIG. 14A schematically depicts a portion of the assembly of FIG. 13 at an intermediate point of fabrication.
FIG. 14B schematically depicts a portion of the assembly of FIG. 13 at an intermediate point of fabrication.
FIG. 14C schematically depicts a portion of the assembly of FIG. 13 at an intermediate point of fabrication.
Figure 15:
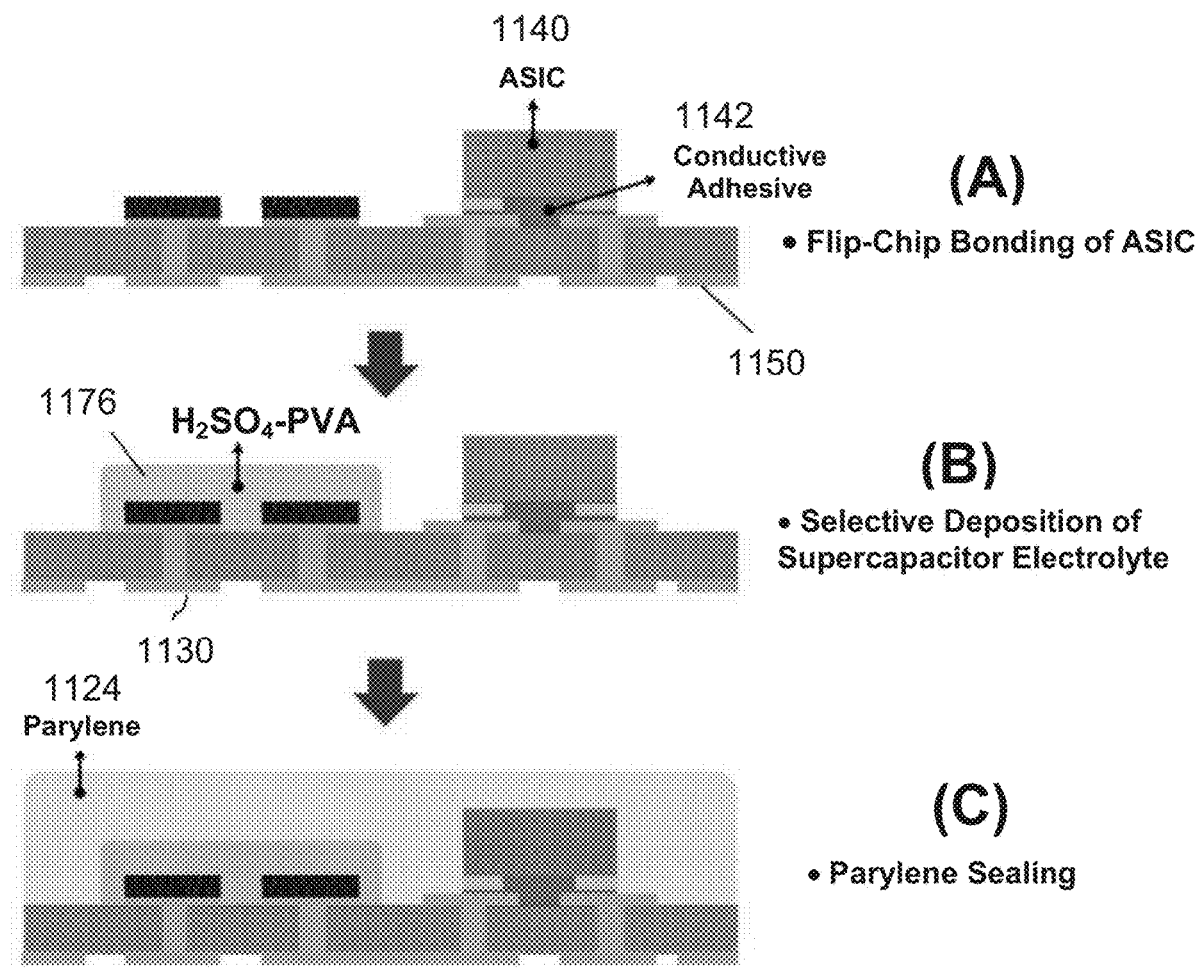
FIG. 15A schematically depicts a portion of the assembly of FIG. 13 at an intermediate point of fabrication.
FIG. 15B schematically depicts a portion of the assembly of FIG. 13 at an intermediate point of fabrication.
FIG. 15C schematically depicts a portion of the assembly of FIG. 13 at an intermediate point of fabrication.

FIGS. 13, 14, and 15 show various aspects of an implantable device with regards to their fabrication. FIG. 13 is a schematic cross sectional representation of an implantable device 1120 according to another embodiment of the present invention. FIG. 13 schematically shows the final assembly. Parylene substrate 1112 includes within it a plurality of vias (four vias shown in FIG. 13), a supercapacitor 1176 and an ASIC 1140 all encased within a parylene structure 1124.

FIG. 14A schematically shows the parylene substrate 1122 that has a plurality of vias or through holes etched or otherwise formed through it. These vias provide pathways for electrical signals to pass from the external surface of device 1120 to the circuitry that is preferably hermetically enclosed within the parylene housing 1124.

FIG. 14B shows a plurality of metallic pads and other devices that are photo lithographically deposited on substrate 1122. An antenna 1150 can be seen extending around the periphery of substrate 1122, it being understood that antenna 1150 may constitute one or more antennas (such as one for reception of power and another for transmission of data), either or both of which can be located internally or externally relative to enclosure 1124. Various other electrical contacts 1130 are shown, some of which provide electrical communication among components mounted on the substrate, and others of which function as the neuromuscular electrodes described herein.

FIG. 14C shows the selective deposition of supercapacitor electrodes. In one embodiment, these electrodes comprise polyaniline (PANI) as an ion absorbing material, although various embodiments of the present invention contemplate yet other ion absorbing materials.

FIG. 15A depicts the bonding of an ASIC 1140 to a conductor in electrical communication with the supercapacitor, and also in electrical communication with an external tissue-contacting electrode. Preferably, a conductive adhesive 1142 bonds ASIC 1140 to the parylene substrate 1122.

FIG. 15B shows the selective deposition of an electrolyte for the supercapacitor. In some embodiments, this electrolyte 1176 includes polyvinyl alcohol and sulfuric acid. FIG. 15C shows a final act of fabrication in which all components are sealed in a parylene housing 1124. Housing 1124 hermetically seals all devices located on substrate 1122 in a biocompatible material. Some of the acts shown in FIGS. 13-15, such as the buildup of housing 1124, are performed using an additive manufacturing method.

Various aspects of different embodiments of the present invention are expressed in paragraphs X1, X2, X3, X4, X5, and X6 as follows:

X1. On aspect of the present invention pertains to an electronic device implantable in an animal. The device preferably includes a radio frequency antenna adapted and configured to transmit an RF signal. The device preferably includes a digital controller transmitting data by said antenna. The device preferably includes a pair of spaced-apart electrodes each in electrical communication with the tissue of the animal and each providing an electrical signal to said controller corresponding to the electrical activity of the tissue. The device preferably includes a source of electrical power to power said controller. The device preferably includes a biocompatible housing encasing most or all of these components X2. Another aspect of the present invention pertains to a method for an electronic device implantable in an animal. The method preferably includes providing a radio frequency antenna, an electrical circuit, an electrical storage device, and a transmitter. The method preferably includes receiving an RF signal at a first predetermined frequency by the antenna. The method preferably includes storing electrical energy received by the antenna in the storage device. The method preferably includes preparing a second RF frequency signal that is a harmonic of the first predetermined frequency. The method preferably includes encoding data from the electrical circuit at the second RF frequency with the transmitter. The method preferably includes transmitting the encoded data with the antenna.

X3. Yet another aspect of the present invention pertains to n electronic device implantable in an animal. The device preferably includes a digital controller wirelessly transmitting data from within the animal. The device preferably includes a wirelessly replenished source of electrical power for powering said controller, said source storing electrical power in a first dielectric-effect capacitor and a second ion absorption-type capacitor. The device preferably includes a biocompatible housing encasing said controller and said source.

X4. Still another aspect of the present invention pertains to a method for an electronic device implantable in an animal. The method preferably includes providing a biocompatible substrate. The method preferably includes placing a pattern of metallic conductors on the substrate. The method preferably includes depositing an ion absorption-type capacitor on a portion of the conductors. The method preferably includes bonding a digital circuit to a portion of the conductors. The method preferably includes encasing the conductors, capacitor, and digital circuit.

X5. In some embodiments, there is an implantable medical device that wirelessly receives power and wirelessly transmits data. The device includes a single antenna that receives power at a predetermined frequency, and transmits data at a harmonic of that frequency. The radiated power is provided more or less continuously. The data is transmitted over relatively short periods. In some embodiments, the power system for the implanted device includes a supercapacitor and a regular capacitor operating in parallel.

X6. Yet another aspect of this invention pertains to an implantable medical device that includes multiple external electrodes. The embodiment preferably includes a kit of devices, with each of the devices having an external shape adapted and configured for delivery by a trochar into the tissue of an animal. Generally, the devices are elongated and smooth externally. Different member devices of the kit have different configurations of placement of a pair of external electrodes. Preferably, at least one of the member devices of the kit has an electrode configuration as shown and described in one of the diagrams of FIG. 8E. Yet another member of the kit corresponds to a different electrode arrangement of FIG. 8E.

Yet other embodiments pertain to any of the previous statements, X1, X2, X3, X4, X5, or X6 which are combined with one or more of the following other aspects. It is also understood that any of the aforementioned X paragraphs include listings of individual features that can be combined with individual features of other X paragraphs.

Wherein said controller includes an application specific integrated circuit.

Which further comprises a rectifier operably connected to said source, wherein said antenna is adapted and configured to receive a radio frequency signal external to the animal and provide the external signal to said rectifier Wherein a part of each said electrode not encased in said housing is in contact with the tissue.

Wherein said housing has a length, and said electrodes are spaced apart by more than about half the length.

Wherein said electrodes are concentric rings.

Which further comprises a trochar having a cylindrical pocket, wherein the shape of said housing is adapted and configured to fit within the pocket.

Wherein said providing includes an antenna, and said receiving is by the antenna and said transmitting is with the antenna.

Wherein said storing is by rectifying the received RF signal.

Wherein the second RF frequency is twice the first predetermined frequency.

Wherein the second RF frequency is a subharmonic of the first predetermined frequency.

Wherein the second RF signal is one half of the first predetermined frequency.

Wherein said first capacitor and said second capacitor are arranged in parallel.

Wherein the time constant of said second capacitor is more than one hundred times the time constant of said first capacitor.

Which further comprises a first radio frequency antenna providing power to said source.

Which further comprises a second radio frequency antenna transmitting the data.

Which further comprises a single radio frequency antenna providing power to said source and transmitting the data.

Wherein said encasing is by additive manufacturing.

Wherein the substrate comprises parylene, and said encasing is with parylene.

Which further comprises depositing an electrolyte on the capacitor before said encasing.

Which further comprises forming vias in the substrate, and said placing includes at least one conductor extends through a via.

Wherein the biocompatible substrate has opposing sides, and said placing is on both sides of the substrate.

Wherein said substrate comprises one of parylene, poly-methyl-methacrylate (PMMA), low-temperature co-fired ceramic (LTCC), and liquid crystal polymer (LCP)

Wherein said encasing is with one of parylene, poly-methyl-methacrylate (PMMA), low-temperature co-fired ceramic (LTCC), and liquid crystal polymer (LCP)

Wherein preparing a second RF frequency signal is by using the first RF frequency.

Wherein said preparing is by providing the first RF signal to a frequency divider.

Wherein said preparing is by providing the first RF signal to a flip-flip.

While the inventions have been illustrated and described in detail in the drawings and foregoing description, the same is to be considered as illustrative and not restrictive in character, it being understood that certain embodiments have been shown and described and that all changes and modifications that come within the spirit of the invention are desired to be protected.

What is claimed is:

1. An electronic device implantable in the muscle of an animal, comprising:
    a near linear radio frequency device antenna adapted and configured to i) transmit an RF signal, and ii) receive wireless power via electric field coupling from a broad-beam external source;
    a digital controller transmitting data by said device antenna;
    a pair of spaced-apart electrodes each adapted and configured to be in electrical communication with a muscle of the animal and each providing an electrical signal to said digital controller corresponding to the electrical activity of the muscle;
    an internal source of electrical power including an internal storage device to power said digital controller; and
    a biocompatible housing encasing said device antenna, said controller, and said internal source, said biocompatible housing encasing the pair of spaced-apart electrodes;
    wherein the electrodes are configured to be placed in close proximity to a nerve and thus detect electromyogram (EMG) signals at a source of the EMG signals and the digital controller is configured to process said EMG signals.

2. The device of claim 1 wherein said digital controller includes an application specific integrated circuit.

3. The device of claim 1 which further comprises a rectifier operably connected to said internal source, wherein said device antenna is adapted and configured to via electric field coupling receive power from the broad-beam external source disposed external to the animal and provide the electric fouled coupled power to said rectifier.

4. The device of claim 1 wherein a part of each said electrode not encased in said housing is configured to be in contact with the muscle.

5. The device of claim 1 wherein said housing has opposing sides, and one electrode of said pair of electrodes is integrated into one side and the other electrode of said pair of electrodes is integrated into the opposing side.

6. The device of claim 5 wherein the electrodes are spaced apart by less than about fifteen millimeters and more than about 1 millimeter.

7. The device of claim 1 wherein said housing has opposing ends, and one said electrode is integrated into one end and the other said electrode is integrated into the opposing end.

8. The device of claim 1 wherein said internal source includes an ion absorption-type supercapacitor.

9. The device of claim 1 wherein said internal source includes a dielectric effect supercapacitor.

10. The device of claim 1 wherein said device antenna receives wireless power via electric field coupling at a first predetermined frequency for providing power to the internal source, and said device antenna transmits data at a frequency different than the predetermined frequency.

11. A method for the use of an electronic device implantable in the muscle of an animal, comprising:
   providing an electrode assembly including an electrical circuit, an electrical storage device, a near linear device antenna, and a transmitter adapted and configured to be implanted in the muscle of an animal;
   receiving wireless power via electric field coupling by the near linear device antenna at a first predetermined frequency from a broad-beam external source;
   storing electrical energy received by the near linear device antenna in the electrical storage device;
   encoding data from the electrical circuit at a harmonic of the predetermined frequency with the transmitter, the harmonic being at a frequency different than the predetermined frequency; and
   transmitting by the near linear device antenna the encoded data, wherein the electrode assembly is configured to be placed in close proximity to a nerve and thus detect electromyogram (EMG) signals at a source of the EMG signals and the transmitter is configured to process said EMG signals.

12. The method of claim 11 wherein said storing is performed by rectifying the received wireless power.

13. The method of claim 11 wherein a pair of electrodes adapted and configured to be in electrical communication with a muscle of the animal and each providing an electrical signal to the electrical circuit corresponding to the electrical activity of the muscle.

14. The method of claim 13 wherein the electrodes are spaced apart by less than about fifteen millimeters.

15. The method of claim 14 wherein the electrodes are spaced apart by more than about one millimeter.

16. The method of claim 11 which further comprises powering the electrical circuit by the storage device.

17. The method of claim 11 wherein the circuit, device, antenna, and transmitter are placed within a housing having an outer shape adapted and configured for implantation into the muscle of an animal, the housing includes a pair electrodes adapted and configured to be in electrical communication with the surrounding muscle, and each said electrode is smoothly integrated into the outer shape.

18. The method of claim 17 which further comprises implanting the housing into the muscle of an animal.

19. The method of claim 11 wherein the electrical storage device includes an ion absorption-type supercapacitor.

20. The method of claim 11 wherein the electrical storage device includes a dielectric effect supercapacitor.

21. An electronic device implantable in the muscle of an animal, comprising:
   a digital controller wirelessly transmitting data from within the animal;
   a wirelessly replenished internal source of electrical power for powering said controller communicating with a near linear radio frequency device antenna adapted and configured to i) transmit an RF signal, and ii) receive wireless power via electric field coupling from a broad-beam external source, said internal source storing electrical power received by the radio frequency device antenna in an ion absorption-type capacitor; and
   a biocompatible housing adapted and configured to be encasing said digital controller and said internal source, said housing having an outer surface and a length; and
   a pair of electrodes each in electrical communication with the muscle tissue of the animal and each providing an electrical signal to said controller corresponding to the electrical activity of the muscle tissue, wherein the electrodes are configured to be placed in close proximity to a nerve and thus detect electromyogram (EMG) signals at a source of the EMG signals and the digital controller is configured to process said EMG signals and transmit the processed EMG signal via the radio frequency device antenna.

22. The device of claim 21 wherein the pair of electrodes are spaced apart by more than about one millimeter and less than about 15 millimeters.

23. The device of claim 21, the electronic device configured to be injectable into a muscle of an animal via a trochar having a pocket, wherein shape of said housing is adapted and configured to fit within the pocket.

24. The device of claim 21 wherein said housing has opposing sides, and one electrode of said pair of electrodes is located on one side and the other electrode of said pair of electrodes is located on the opposing side.

25. The device of claim 21 wherein said housing has opposing ends, and one electrode of said pair of electrodes is located on one end and the other electrode of said pair of electrodes is located on the opposing end.

26. The device of claim 21 wherein the pair of electrodes are spaced apart by less than about fifteen millimeters.

27. The device of claim 26 wherein the pair of electrodes are spaced apart by more than about one millimeter.

28. The device of claim 21 which further comprises a rectifier operably connected to said internal source, wherein said device antenna provides the received wireless power via electric field coupling to said rectifier.

29. The device of claim 21 wherein said device antenna receives wireless power via electric field coupling at a first predetermined frequency for providing power to said internal source, and said device antenna transmits data at a a frequency different than the predetermined frequency.

30. An electronic device implantable in the muscle of an animal, comprising:

a near linear radio frequency device antenna adapted and configured to i) transmit an RF signal, and ii) receive wireless power via electric field coupling from a broadbeam external source;

a digital controller transmitting data by said device antenna;

a pair of electrodes each in contact with and each in electrical communication with a muscle of the animal and each in electrical communication with said controller;

an internal source of electrical power to power said digital controller;

a rectifier operably connected to said internal source, wherein said device antenna is adapted and configured to convey received coupled power from the external source to said rectifier; and a biocompatible housing having an outer surface adapted and configured for implantation by injection, and wherein the electrodes are configured to be placed in close proximity to a nerve and thus detect electromyogram (EMG) signals at a source of the EMG signals and the digital controller is configured to process said EMG signals.

31. The device of claim 30 wherein said digital controller includes an application specific integrated circuit.

32. The device of claim 30 wherein the electronic device is configured to be injectable via a trochar having a pocket, wherein the shape of said housing is adapted and configured to fit within the pocket.

33. The device of claim 30 wherein said housing has opposing sides, and one electrode of said pair of electrodes is located on one side and the other electrode of said pair of electrodes is located on the opposing side.

34. The device of claim 33 wherein the electrodes are spaced apart by less than about fifteen millimeters and more than about 1 millimeter.

35. The device of claim 30 wherein said housing has opposing ends, and one electrode of said pair of electrodes is located on one end and the other electrode of said pair of electrodes is located on the opposing end.

36. The device of claim 35 wherein the electrodes are spaced apart by more than about one millimeter and less than about 15 millimeters.

37. The device of claim 30 wherein said device antenna receives the wireless power via electric field coupling at a first predetermined frequency for providing power to said internal source, and said device antenna transmits data at a frequency different than the predetermined frequency.

38. The device of claim 30 wherein said internal source includes an ion absorption-type capacitor.

39. The device of claim 30 wherein the internal source includes a dielectric effect supercapacitor.

* * * * *